tion-in-part of application No. 13/177,402,
filed on Jul. 6, 2011.

(12) United States Patent
Seppi et al.

(10) Patent No.: US 10,602,991 B2
(45) Date of Patent: Mar. 31, 2020

(54) FUNCTIONAL AND PHYSICAL IMAGING USING RADIATION

(75) Inventors: Edward J. Seppi, Portola Valley, CA (US); Renate Parry, Oakland, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

(21) Appl. No.: 13/434,689

(22) Filed: Mar. 29, 2012

(65) Prior Publication Data

US 2013/0010927 A1 Jan. 10, 2013

Related U.S. Application Data

(63) Continuation-in-part of application No. 13/177,402, filed on Jul. 6, 2011.

(51) Int. Cl.
*A61B 6/03* (2006.01)
*A61B 6/00* (2006.01)
*A61B 6/06* (2006.01)
*A61N 5/10* (2006.01)
*G21K 1/02* (2006.01)

(52) U.S. Cl.
CPC ............. *A61B 6/032* (2013.01); *A61B 6/037* (2013.01); *A61B 6/06* (2013.01); *A61B 6/4071* (2013.01); *A61B 6/4085* (2013.01); *A61B 6/4233* (2013.01); *A61B 6/4241* (2013.01); *A61B 6/4291* (2013.01); *A61B 6/483* (2013.01); *A61B 6/50* (2013.01); *A61B 6/504* (2013.01); *A61B 6/507* (2013.01); *A61B 6/4007* (2013.01); *A61B 6/481* (2013.01); *A61N 5/1048* (2013.01); *G21K 1/025* (2013.01)

(58) Field of Classification Search
CPC .............................. A61B 6/485; G01N 23/223
USPC .................................................. 600/436, 407
See application file for complete search history.

(56) References Cited

U.S. PATENT DOCUMENTS

| 4,856,043 | A | * | 8/1989 | Zola | ............................... 378/149 |
| 4,969,175 | A | * | 11/1990 | Nelson | ................... B82Y 10/00 378/146 |
| 5,729,582 | A | * | 3/1998 | Ham et al. | ....................... 378/89 |
| 6,122,344 | A | | 9/2000 | Beevor | |
| 6,895,074 | B2 | * | 5/2005 | Benedetti | ......................... 378/89 |
| 7,203,276 | B2 | | 4/2007 | Arsenault et al. | |

(Continued)

OTHER PUBLICATIONS

Harding, G. "Inelastic photon scattering: effects and applications in biomedical science and industry". Radiation Phys. Chem. 50, pp. 91-111 (1997).*

(Continued)

*Primary Examiner* — Angela M Hoffa
*Assistant Examiner* — Helene Bor
(74) *Attorney, Agent, or Firm* — Vista IP Law Group, LLP

(57) ABSTRACT

An apparatus to examine a target in a patient includes an x-ray source configured to deliver a first x-ray beam towards the target, a device having an array of openings, the device located at an angle less than 180 degrees relative to a beam path of the first x-ray beam to receive a second x-ray beam resulted from an interaction between the first x-ray beam and the target, and a detector aligned with the device, the detector located at an angle less than 180 degrees relative to the beam path of the first x-ray beam to receive a part of the second x-ray beam from the device that exits through the openings at the device.

50 Claims, 15 Drawing Sheets

(56) References Cited

U.S. PATENT DOCUMENTS

| | | | | |
|---|---|---|---|---|
| 2004/0092807 | A1* | 5/2004 | Breskin | A61B 6/00 600/407 |
| 2005/0117697 | A1* | 6/2005 | Yasunaga | A61B 6/032 378/19 |
| 2006/0182217 | A1* | 8/2006 | Harding et al. | 378/44 |
| 2007/0218556 | A1* | 9/2007 | Harris | G01N 21/274 436/25 |
| 2008/0159474 | A1 | 7/2008 | Hubbard-nelson et al. | |
| 2008/0253522 | A1 | 10/2008 | Boyden | |
| 2009/0067572 | A1* | 3/2009 | Grodzins et al. | 378/45 |
| 2009/0086905 | A1* | 4/2009 | Boyden et al. | 378/46 |
| 2009/0274268 | A1* | 11/2009 | Grodzins | A61B 6/482 378/45 |
| 2010/0310046 | A1* | 12/2010 | Connor et al. | 378/85 |

OTHER PUBLICATIONS

Dutta, Joyita et al., "Joint L1 and total variation regularization for fluorescence molecular tomography", Physics in Medicine and Biology, Phys. Med. Biol. 57, (2012) IOP Publishing, pp. 1459-1476.

Schlomka, J P et al., "Experimental feasibility of multi-energy photon-counting K-edge imaging in pre-clinical computed tomography" Physics in Medicine and Biology, Phys. Med. Biol. 53, (2008) IOP Publishing, pp. 4031-4047.

Final Office Action dated Jun. 10, 2013 for U.S. Appl. No. 13/177,402.
Non-final Office Action dated Oct. 7, 2014 for U.S. Appl. No. 13/177,402.
Final Office Action dated Jan. 15, 2015 for U.S. Appl. No. 13/177,402.
Final Office Action dated Dec. 4, 2015 for related U.S. Appl. No. 13/177,402.
Non-final Office Action dated May 3, 2016 for related U.S. Appl. No. 13/177,402.
Final Office Action dated Dec. 23, 2016 for related U.S. Appl. No. 13/177,402.
Advisory Action dated Apr. 6, 2017 for related U.S. Appl. No. 13/177,402.
Non-Final Office Action dated Oct. 20, 2017 for related U.S. Appl. No. 13/177,402.
Final Office Action dated Jun. 7, 2018 for related U.S. Appl. No. 13/177,402.
Non-Final Office Action dated Oct. 9, 2018 for related U.S. Appl. No. 13/177,402, 16 pages.
Final Office Action dated May 24, 2019 for related U.S. Appl. No. 13/177,402.
Advisory Action dated Aug. 5, 2019 for related U.S. Appl. No. 13/177,402.
Non-Final Action dated Oct. 9, 2019 for related U.S. Appl. No. 13/177,402.
Non-final Office Action dated Oct. 15, 2012, for U.S. Appl. No. 13/177,402.
Non-final Office Action dated Apr. 23, 2015 for U.S. Appl. No. 13/177,402.

* cited by examiner

FUNCTIONAL AND PHYSICAL IMAGING USING RADIATION

RELATED APPLICATION DATA

This application is a continuation-in-part of U.S. patent application Ser. No. 13/177,402, filed on Jul. 6, 2011, the entire disclosure of which is expressly incorporated by reference herein.

FIELD

This application relates generally to apparatus, system, and methods for medical imaging and, more specifically, to a new technique for x-ray medical imaging and functional evaluation.

BACKGROUND

There are many medical imaging techniques currently used for diagnosis, include computerized tomography (CT), nuclear spectroscopy, magnetic resonance imaging (MRI), positron emission tomography (PET), which can provide the non-invasive medical image of a target in the patient. Some of the above techniques require radioactive imaging agents to be used in conjunction, such as PET. The radioactive imaging agents interact with the tissue(s) in the target region of the patient, thereby allows the tissue(s) that contains the agent to be detected using a detector.

The x-ray based imaging techniques, such as CT, detects the x-rays penetrated, attenuated, and/or scattered by the target region, on a medium that is opposite of the x-ray source, such as x-ray sensitive film or photonic detector. These x-ray based imaging techniques, however, do not account for all of the photons directed at the target region. Applicant of the subject application determines that secondary x-ray beams, such as scattered x-ray, may hold valuable imaging data that has not been utilized.

SUMMARY

In accordance with some embodiments, an apparatus to examine a target in a patient includes an x-ray source configured to deliver a first x-ray beam towards the target, a device having an array of openings, the device located at an angle less than 180 degrees relative to a beam path of the first x-ray beam to receive a second x-ray beam resulted from an interaction between the first x-ray beam and the target, and a detector aligned with the device, the detector located at an angle less than 180 degrees relative to the beam path of the first x-ray beam to receive a part of the second x-ray beam from the device that exits through the openings at the device.

In accordance with other embodiments, a method to image a target includes directing a first x-ray beam generated from an x-ray source towards the target, wherein a second x-ray beam is generated by an interaction of the first x-ray beam with the target, detecting the second x-ray beam using a detector that is placed at less than 180 degrees relative to a path of the first x-ray beam, and obtaining quantum property for the target using the detected second x-ray beam.

In accordance with other embodiments, an apparatus for determining a characteristic of a target includes a processing unit configured to receive first quantum data from a first detector element of a detector, the first quantum data corresponding to a first part of the target, receive second quantum data from a second detector element of a detector, the second quantum data corresponding to a second part of the target, identify first k-alpha peak, first k-beta peak, and first Compton scatter peak from the first quantum data, identify second k-alpha peak, second k-beta peak, and second Compton scatter peak from the second quantum data, and calculate a parameter using the first k-alpha peak, the first k-beta peak, the first Compton scatter peak, the second k-alpha peak, the second k-beta peak, the second Compton scatter peak, or a combination thereof.

Other and further aspects and features will be evident from reading the following detailed description of the embodiments.

BRIEF DESCRIPTION OF THE DRAWINGS

The drawings illustrate the design and utility of various embodiments of the present application, in which similar elements are referred to by common reference numerals. In order to better appreciate how advantages and objects of the present application are obtained, a more particular description will be rendered by reference to specific embodiments thereof, which are illustrated in the accompanying drawings. Understanding that these drawings depict only typical embodiments and are not therefore to be considered limiting of its scope. The present application will be described and explained with additional specificity and detail through the use of the accompanying drawings in which.

DETAILED DESCRIPTION

Figure 1:
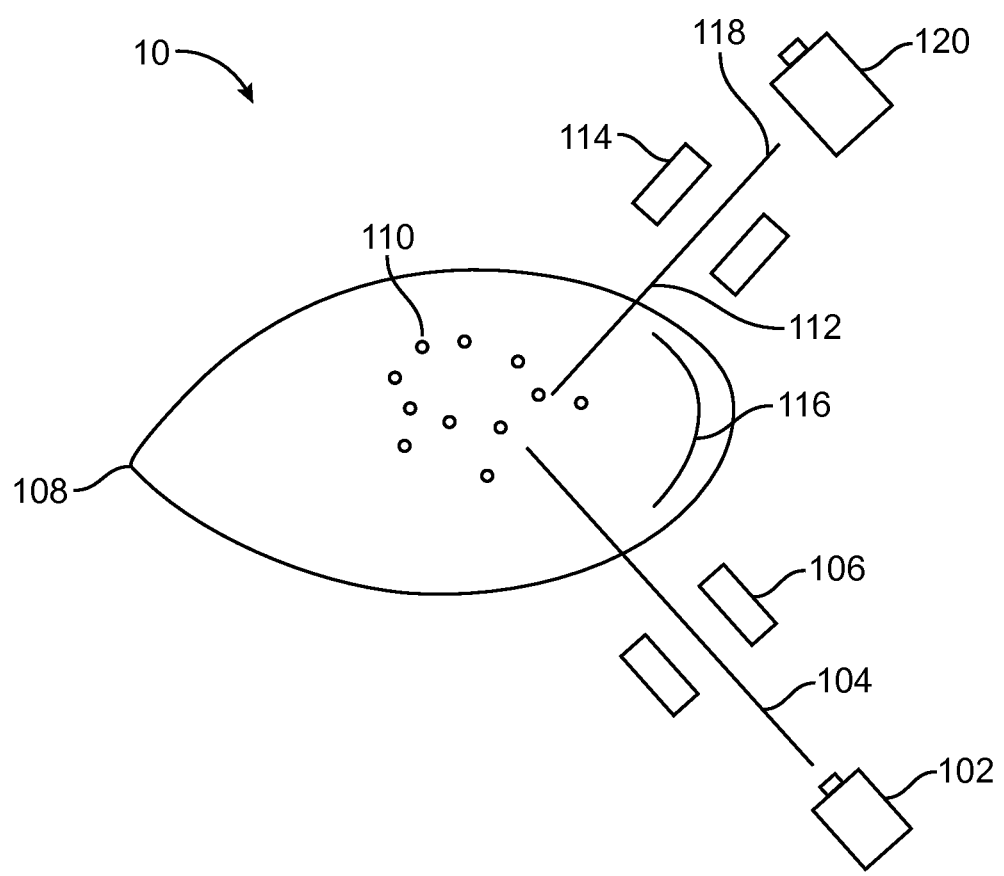
FIG. 1 is a schematic illustrating an apparatus of scatter x-ray detection in accordance with some embodiments.

Various embodiments of the present application are described hereinafter with reference to the figures. It should be noted that the figures are not drawn to scale and elements of similar structures or functions are represented by like reference numerals throughout the figures. It should also be noted that the figures are only intended to facilitate the description of specific embodiments. They are not intended as an exhaustive description of the present application or as a limitation on the scope of the present application. In addition, an aspect or a feature described in conjunction with a particular embodiment is not necessarily limited to that embodiment and can be practiced in any other embodiments of the present application.

This application provides for an apparatus and a method to measuring the spatial distribution, temporal attributes, and/or functional attributes of a material of interest. Unlike apparatus and methods that measure photonic information received directly opposite of the x-ray source, which measures the x-ray photons travelling through the material of interest, embodiments of the apparatus and method described herein measure the x-ray photons that are scattered or generated by the incident x-ray photons in the material of interest (such as tissue). Embodiments of the system and method described herein uses incidental excitation radiation from a source external to the material of interest, which may include the target tissue and/or an agent such as injected contrast agent and/or implanted objects, to produce secondary radiation having different characteristics and different beam paths from the incident radiation. This secondary radiation, having different attributes from that of the incident radiation, is produced by interaction of the incident radiation with the tissue and/or an agent such (as contrast agent, implanted material, or combination thereof). The secondary radiation is detected external to the material of interest, and may be analyzed to determine its source location, directionality, type, spatial distribution, or other attributes. Information about the incident radiation and detected secondary radiation (both of which may be of more than one type) may be used to determine positional, geometric, functional attributes, and temporal attributes of the material of interest. The spatial distribution may include the existence, density, location, function, and shape of the material of interest in the target volume being studied. The temporal attributes (which may be obtained by continuous monitoring or monitoring the same point of interest over different points in time) may include the rate of build-up and clearance, the pattern of flow, changes in existence of, density, location, function, shape and location of material nodules, and other attributes of the various types of molecules present in the material of interest. An example of detecting such temporal attributes may be accomplished by observing the change of the various types of molecules present over time (e.g., measuring the change of the amount of glucose in the tissue over time). The functional attributes may be determined by simultaneous observation of two or more attributes, such as by observing two or more types of secondary radiation emitted from the material of interest, projecting two or more types of excitation radiation onto the material of interest, injecting two or more types of contrast agent or tissue, or any combination thereof. For example, in some embodiments, functional attributes may be determined by observing the change in ratio or the function of two different types of tissue or structure (e.g., tissue, fat, bone, lung, angiogenesis liquid, solid) at a point of interest over time represents one or more human body function(s)) in the material of interest. The detected spatial distribution, temporal attributes and functional attributes can be arbitrarily combined in some embodiments.

Embodiments described herein involve using an incidental excitation x-ray radiation that interacts with material of interest, which may include tissue and/or an agent (e.g., iodine contrast agent, gadolinium, gold, bismuth) in a target volume. In other embodiments, instead of using x-ray radiation, other types of beams, such as a proton beam, may be used. Thus, as used in this specification, the term "radiation" is not limited to x-ray radiation, and may refer to other types of beam that radiate, such as a proton beam. High Z elements or elements with high electron density that are naturally occurring in tissues may also act as an agent in some embodiments. The spatial, temporal, and functional attributes can be determined using: a) photo absorption of incidental excitation x-ray beam and subsequent emission of characteristic photons (e.g., K-alpha and K-beta radiation) by the material of interest, as well as b) secondary radiation generated from Compton scatter of incidental excitation x-ray beam interacting with tissue.

Embodiments of the apparatus and method described herein involve using an excitation beam that interacts with material of interest to generate a secondary radiation. The material of interest includes an atom or a particle in target tissue with which the incident radiation interacts. In some embodiments, the material of interest may be a particle occurred naturally in the tissue. In such cases, the excitation beam interacts with the atoms and electrons in the tissue itself. These interactions yield secondary radiation which can be measured to determine various information. The information can be used either alone, or with information obtained using an agent, such as a contrast.

In other embodiments, the material of interest may be an agent (or more than one agent) externally introduced into the tissue for enhancement of detection. The agent may be particle(s) or fluid. By means of non-limiting examples, the agent may be administered to the patient using various methods, such as by injection, absorption, implant, or attachment (e.g., a material attached to a molecule, which through body function, attaches itself to cancer, hypoxic tissue, a particular tissue etc.). The agent may be any material other than the tissue. An exemplary agent would be a contrast agent that has properties suitable for detection such that if the external radiation is an x-ray radiation at an appropriate energy level, the external radiation will interact with the agent to produce photo absorption-emission radiation and Compton scatter radiation.

In further embodiments, the material of interest may be both tissue and an agent.

In still further embodiments, the material of interest may be an atom of a particle in a non-biological volume to be examined.

As discussed, the incident radiation interacts with material of interest in a manner where the measured spatial, functional and/or temporal data may provide important information. The excitation beam (or incidental beam) is a radiation beam with sufficient intensity (number of photons) and specific radiation quantum attributes (e.g., quantum energy (such as photon energy), quantum spectrum (such as number of photons in a small band of energy found in the beam), and other properties (such as polarization of the radiation), which may be quasi-monoenergized, collimated, directed, and/or controlled. The source of the excitation beam is external to the material of interest and is directed to pass into the material of interest. For example, the radiation is optionally quasi mono-energetic and at a suitable quantum energy. Such quasi mono-energetic radiation can be created by x-ray treated with crystal diffraction that may be shaped into a pencil beam, a fan beam, flood beam, a cone beam, and other arbitrarily shaped beams. In other embodiments, proton beam, neutron beam, or other particle beams may be used as the excitation beam. In some embodiments, the excitation beam may be generated using crystal (in the radiation source) to create a refracted beam at an angle. By adjusting the angle, the excitation beam with a certain desired energy level may be generated. The orientation of the crystal in the radiation source may be adjusted in some embodiments.

The secondary radiation is radiation generated as a result of interaction of the excitation radiation with the material of interest. This secondary radiation is externally detected and analyzed to determine the source location, directionality, temporal, and/or type attributes of the material of interest. In some embodiments, the secondary radiation is detected with apparatus which may be collimated to sense its directionality and different aspects of the radiations attribute (e.g., intensity (such as number of photons), energy (such as photon energy), spectrum (such as number of photons in a small band of energy found in the beam), and other attributes, such as the "spin" or polarization of the radiation). Any of the foregoing examples may be considered a quantum property or quantum data. As an example, the secondary beam may be collimated which defines the attributes of cross sectional size and shape, and the direction for the scattered x-ray photons to be analyzed. In some embodiments, the beam's energy signature may be determined by x-ray spectrum analysis. Information about beam energy spectrum and/or the energy of particular photons may be used to evaluate attributes of the material of interest. In some embodiments, if proton beam is used as the excitation beam, the secondary radiation of interest maybe generated by nuclear decays.

Embodiments of the system described herein include a photon detection system. In some embodiments, the detection system may include an array of spectrum sensitive x-ray detectors for analysis of the scattered photons. In other embodiments, the detection system may also have collimation directivity control and/or photon energy spectrum analysis capability, but the system is not limited to the exemplary capabilities it may have. Also, in any of the embodiments described herein, the system may further include a calibration and correction apparatus for performing calibration and correction procedures to attain results of good accuracy. Furthermore, in any of the embodiments described herein, the system also includes a processor (which may be implemented using a computer) for analyzing the acquired signals.

FIG. 1 illustrates a system 10 in accordance with some embodiments. The system 10 includes a radiation source 102, an incidental collimator 106, an exit beam collimator 114, and a spectrum sensitive photon detection system 120. The radiation source 102 is configured to provide an excitation beam 104. The excitation beam 104 from a radiation source 102 is directed toward a material of interest 110 within a target volume 108. Optionally, there can be two or more target volumes in the path of the excitation beam. There can also be more than one materials of interest within one or more target volume in the path of the excitation beam. The excitation beam 104 is optionally collimated by incidental collimator 106 and the secondary radiation 112 (e.g., resulted from the photoelectric and Compton interactions) is detected and analyzed. Secondary radiation 112, which travels in directions different from that of the incident excitation beam (e.g., at an angle 116) and have a different quantum energy, is produced from the excitation beam 104 interacting with the material of interest 110. For the secondary radiation produced by photoelectric effect, the quantum energy of the secondary x-ray is highly dependent on the property of the atom (e.g., the atomic number) that the incident excitation beam impinges upon. For the secondary radiation produced by Compton effect, the interaction is primarily with the electrons in the material. The secondary quantum energy is dependent on the scatter angle. The excitation beam may impinge upon the atom of the normal tissue, and/or the imaging agent, or their respective constituent electrons. For the secondary radiation produced by Compton scatter effect, the quantum energy of the secondary x-ray is dependent on electron constituents of the material of interest and the angle at which the secondary x-ray is detected. As an example, the secondary x-rays are emitted and detected at an angle 116, which may be approximately 30 to 170 degrees relative to the path of excitation beam 104. The secondary x-rays 112 may be collimated by exit beam collimator 114, and the collimated analysis beam 118 is detected and analyzed. The combination of collimators 106 and 114 defines the target volume from which the secondary radiation is emitting. The analysis beam 118 may be measured by the spectrum sensitive photon detection system 120. In some embodiments, the analysis beam 118 may include photons which are primarily produced by the excitation x-ray beam interacting with the material of interest in the target volume defined by collimators 102 and 114. In other embodiments, the system 10 may not include either or both of the collimators 106, 114.

An embodiment to examine a target volume of tissue using the system 10 will now be described. The location and shape of the target volume may be defined by the effective crossing point and cross sectional area of the pencil incident beam and the detected envelope. For example, with respect to FIG. 1, the incident collimation 106 defines a cross section of the incident radiation beam which represents a surface through which the incident radiation passes. The exit beam collimation 114 defines another surface through which the exit radiation must pass. These two surfaces may intersect to form an enclosed volume. This may define a target volume in some embodiments, which has a location and a shape. In some embodiments, one or more incident pencil beams, one or more secondary detection envelopes, and one or more target volumes may be used. In some cases, the detection envelope may have a detection area that is larger than the cross section of the geometric detection pencil. The detection envelope (region) may include detection envelopes such as secondary radiation spectrum (quantum intensity in envelopes of energy), and secondary quantum polarization. Either one of these property may be considered example of quantum property or quantum data. Various sources and detector envelopes are possible in different embodiments. A source envelope maybe an incident beam having quasi mono-energetic x-rays with some central energy, or two or more different central energies. It may be polarized or un-polarized, coherent or incoherent, pulsed or continuous. Also, in some embodiments, the sensitivity envelope of the detector maybe energy sensitivity, polarization sensitivity, etc.

Figure 2B:
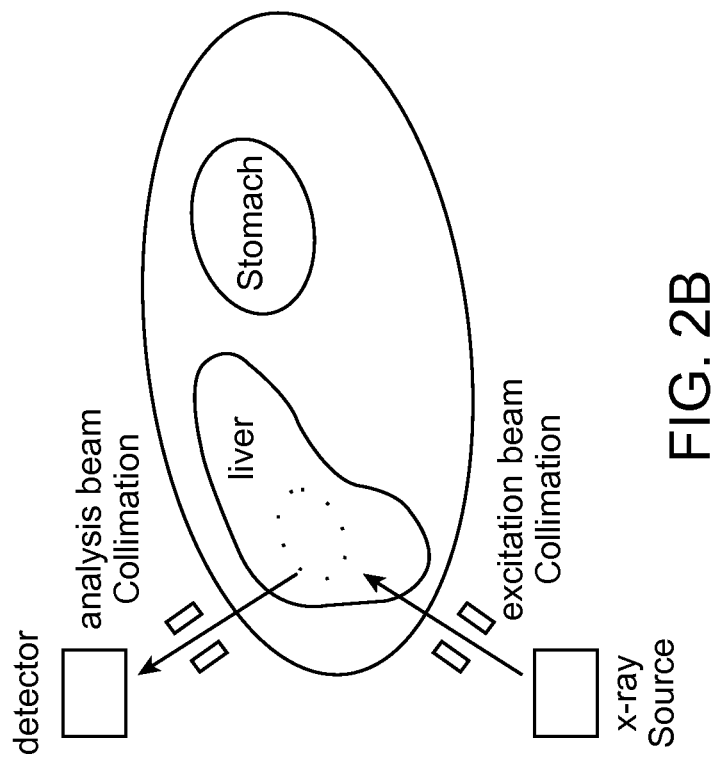
FIG. 2B is a schematic illustration of imaging a volume of abdominal tissue in accordance with some embodiments.
Figure 2A:
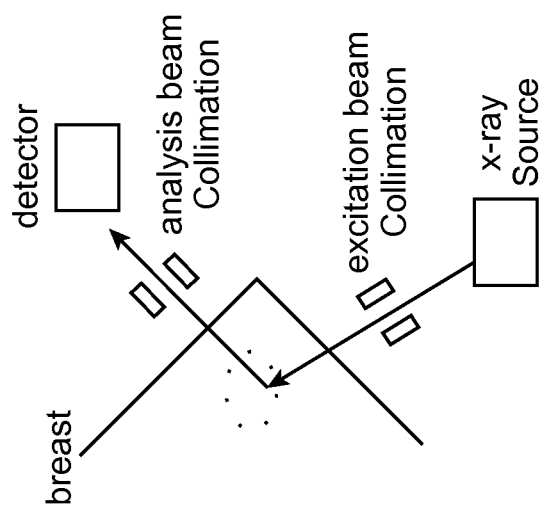
FIG. 2A is a schematic illustration of imaging a volume of breast tissue in accordance with some embodiments.

An imaging agent may be optionally administered in the target volume. If an imaging agent is not administered, the measurement depends on the different materials naturally occur in the target volume. The volume may be the breast (or breast with chest wall), liver, prostate, kidney, lung, or other anatomical site of interest (an embodiment to examine breast is shown in FIG. 2A and another embodiment to examine abdomen is shown in FIG. 2B). In general, an excitation beam is arranged to target a voxel in the site of interest, and secondary beams originate from the voxel are generated after the photons from the excitation beam interact with the voxel. The interactions that generate secondary beams are: 1) the photo absorption and photo emission (also known as photo absorption and emission radiation, or photo secondary radiation) by one of the constituents of the voxel (e.g., the constituent(s) may be an agent, or otherwise a naturally occurring material); and 2) the Compton scattering of the x-ray photons by the electron constituents of the voxel.

Figure 3:
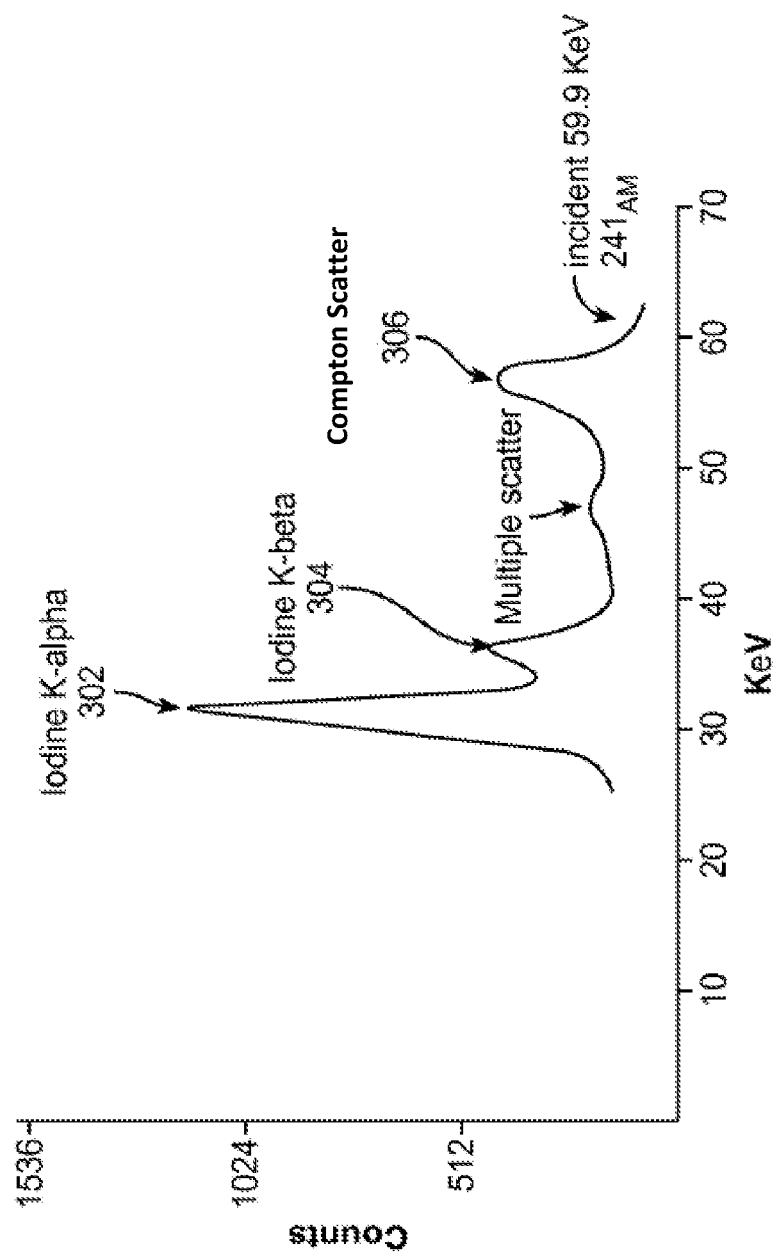
FIG. 3 is an example of an energy spectrum diagram generated using an $^{241}$Am source with $^{123}$I imaging agent in accordance with some embodiments.

During use of the system 10, the excitation beam 104 is directed to the target region, and secondary beam 112 (which in various embodiments may or may not be collimated), is then detected by the detector 120. The detector 120, which may be a quantum energy sensitive counting detector, is configured to provide signals to a processor (coupled to the detector 120) in response to the detected secondary beam 112. The processor is configured to create an energy spectrum using the signals from the detector 120. In some embodiments, the signals from the detector 120, and information (such as the spectrum) generated by the processor may be stored in a non-transitory medium for later processing, and/or may be displayed in a screen for allowing a user to examine the data. The energy spectrum of a voxel administered with $^{123}$I showing both interactions (photo absorption and emission, and Compton scattering) is shown in FIG. 3. As discussed, photo absorption and photo emission by the imaging agent contribute to the creation of the secondary beams 112. As the photons from the excitation beam 104 are absorbed by the atoms of the imaging agent, the electrons of the atoms are elevated to an excited state (photo absorption) followed by rapid decay and emission of radiation photons (photo emission). The emitted radiation photons exhibit the energy characteristics of the excited atom. For example, if the administered agent is iodine and the energy of the excitation beam is at ~59.9 keV from an $^{241}$Am source in the radiation source 102, the energies of the fluorescence radiation photons K-alpha 1 (shown as peak 302 in FIG. 3) and K-beta 1 (shown as peak 304 in FIG. 3) from photo interaction of the incident radiation with the Iodine are ~28.7 keV and 32.4 keV, respectively. The excitation beam 104 also interacts with the atoms of the tissue (e.g., breast tissue, or any of other types of tissue), but since the atomic number of the atoms of the tissue is lower, the emitted photons have the energy of <10 keV. The emitted radiation photons are emitted in all directions.

Thus, as illustrated above, based on the values of the energy of the fluorescence radiation photons in the graph, the material in the target region may be identified (because different materials may produce different unique energy levels for the photonic energy Ep).

Also, as discussed, Compton Scatter of the x-ray photons by the electron constituents of the voxel is another phenomenon that contributes to the creation of the secondary radiation in the secondary beam 112. The phenomenon of Compton Scatter is well known in the art. In general, the x-ray photons interact with the constituents (e.g., electrons) in the voxel (in presence or absence of the agent), and are scattered in new directions and lose energy in the process. The number of electrons in the voxel is not significantly changed by the presences or absence of the agent. The energy of the scattered photons is dependent on the scatter angle, which can be calculated by the following equation:

Energy of Scatter Photon $Ec$=0.51 MeV/((1−cos (scatter angle))+(0.51 MeV/Energy of Incident Photon))

In the above equation, the scatter angle is the angle between the path of incident beam 104 and the path of scatter beam 112. All of the Compton scattered radiation in a cone with its axis in the direction of the incident pencil beam have the same energy quantum energy since the scatter angle is the half angle of the cone. For example, if the incident photons have the energy of ~60 keV, using the information above, the energies Ec of Compton scattered photons (shown as peak 306 in FIG. 3) for scatter angles 75 degrees, 90 degrees, and 105 degrees are 55.1 keV, 53.6 keV, and 52.2 keV respectively.

Also, in some embodiments, a processor (coupled to the detector 120 for receiving data from the detector 120) may be configured to determine the ratio Ep/Ec from the graph (wherein Ep is photonic energy, and Ec is energy of Compton scattered photons). As an example, if iodine is used as the agent, then the ratio Ep/Ec correlates with the ratio of iodine mass/tissue mass at the target region. In some cases, the ratio Ep/Ec may be calculated at every prescribed time interval (e.g., every 1-2 seconds), and the resulting ratios may be stored in a non-transitory medium for later processing. For example, the ratios may be presented in a plot of time (in the x-axis) versus ratio (in the y-axis), which may be displayed in a screen. The plot may be used to examine leakage of the agent at the target region (e.g., how fast the agent at the target region is leaking).

Figure 4:
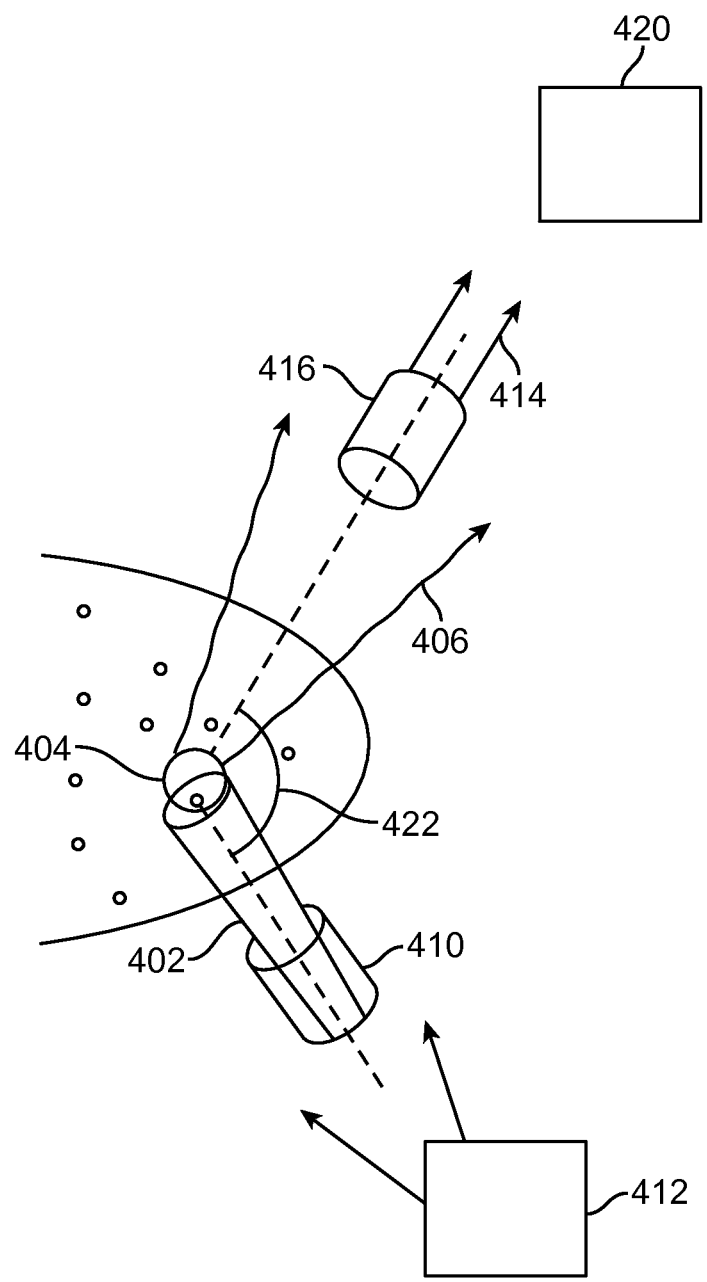
FIG. 4 is a schematic illustration of an example of a pencil beam source as the radiation source and pencil secondary beam detection mode in accordance with some embodiments.
Figure 5:
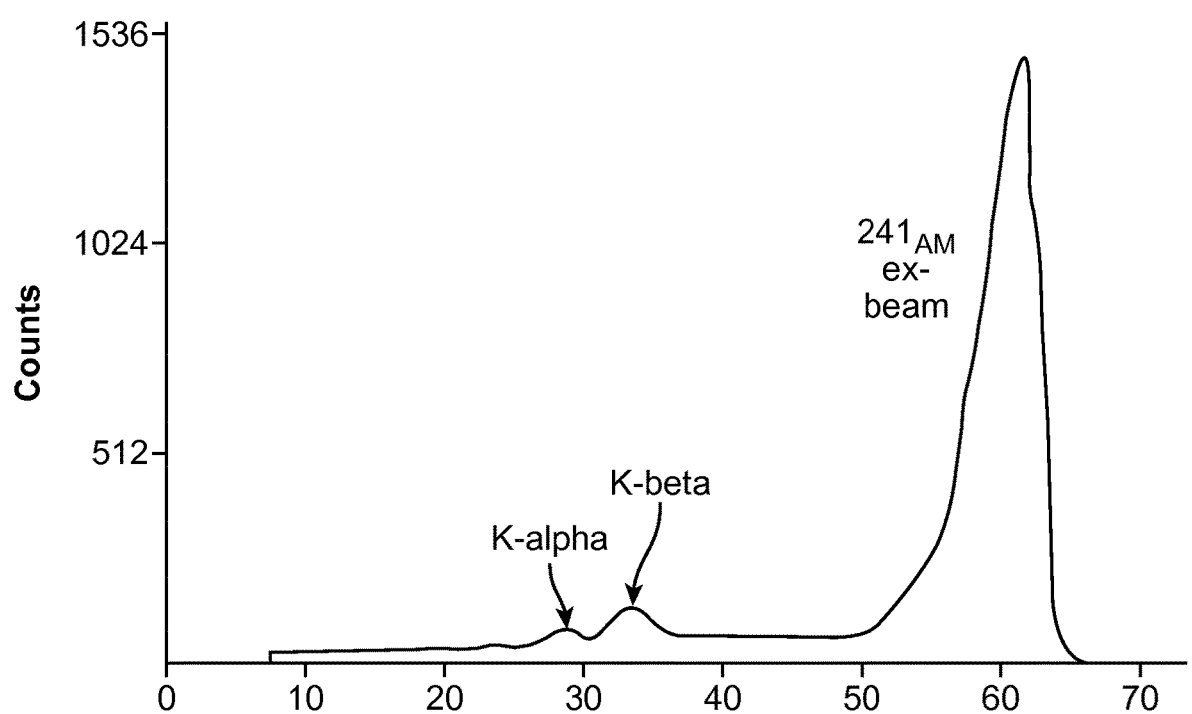
FIG. 5 is an example of an incident beam detected spectra of photo-absorption and emission using an $^{241}$Am source in accordance with some embodiments.

In any of the embodiments described herein, the excitation beam 104 may be a pencil beam, and the secondary beam may also be a pencil beam (excitation pencil beam-secondary pencil beam detection mode). Also, in some embodiments, other shaped incident and exit beams may be achieved as groups of multiple pencil beams leading to any desired shape for the incident collimation and/or exit collimation. FIG. 4 illustrates a detection system that utilizes excitation pencil beam and detected secondary pencil beam in accordance with some embodiments. In this embodiment, the excitation beam is emitted from x-ray source 412 (which may be an example of the source 102 of FIG. 1) and collimated to circular or rectangular shape by a first collimator 410 (which may be an example of the collimator 106 of FIG. 1) having nominal diameter (e.g., ~2 mm, 3 mm, etc.), which may be referred to as pencil beam. The excitation pencil beam 402 may have monochromatic or multi-chromatic spectral characteristics. The source 412 includes an electronic x-ray generated by an x-ray tube and crystal diffraction apparatus, which may be a quasi-monoenergetic source generated by an electronic device or it may be radioactive substance. This configuration allows the quantum energy and the intensity of the pencil beam 402 to be arbitrarily selected, and the spectral characteristics to be optimized. As an example, FIG. 5 shows the spectral distribution of an excitation beam using $^{241}$Am as the radiation source 412, measured with an energy sensitive HgI detector system (or may also be a CdTe detector or a detector having any of other energy sensitive photon sensing materials), which can detect x-ray photons with multiple energy levels. In other embodiments, the radiation source can be other materials.

Returning to FIG. 4, the secondary beams 406 are generated by interaction of the excitation beam 402 with a voxel 404 (e.g., a volume of tissue and/or imaging agent optionally administered within the target volume). The voxel 404 and its location is defined by the intersection of the excitation beam 402 and the secondary beam 406 within the target volume. In this example the secondary beams 406 are generated in a way that is similar to a light bulb radiating light in all directions. The voxel 406 may be "viewed" by collimation of the secondary beam 406 at by a second collimator 416 (which may be an example of the collimator 114 of FIG. 1) down to size of pencil beam (secondary analysis beam 414) and analyzed by the detector 420 (which may be an example of the detector 120 of FIG. 1). The collimated secondary beam may have a circular cross section, a rectangular cross section, or any of other shapes. Also, in some embodiments, the collimated secondary beam may have a cross sectional size of ~2 mm, ~3 mm, or any of other dimensions. Essentially, only a sample of the secondary radiation is analyzed.

The source incident beam 402 and the detected secondary beam 414 may be adjusted (e.g., scaled, positioned, shaped, etc.) to view voxels of various shapes, sizes, and locations through adjustment of collimation (410 and/or 416), source 412, and/or the size of the detector 420. The detector 420 may detect photons with different quantum energy levels and is placed at an angle 422 relative to the excitation beam source 412 (e.g., the angle between the path of the excitation beam 402 and the path of the secondary radiation 414).

The secondary analysis beam 414 has primarily two components. One of which is the scattered beam generated from photo absorption of the excitation pencil beam 402 by the imaging agent. The photo scattered beam has intensity that is proportional to the amount of imaging agent in the voxel, density of materials of the voxel, and intensity of the excitation beam 402. The photo scattered beam's quantum energy spectrum is dependent on the atomic number of materials in the voxel. Another component of the secondary radiation 414 is the Compton scatter radiation, which may be detected by the multi-energy detector in addition to the scattered beam. The Compton scatter is primarily dependent of the electron density in the voxel. Its quantum energy spectrum depends on the angle of scatter and incident beam quantum energy spectrum. In some embodiments, spatial and temporal information may be derived from detected secondary beams 414, which are analyzed to produce medical image for diagnostic and/or treatment. To acquire sufficient data for volumetric spatial and temporal information, the excitation beam 402 may raster scan the entire target volume voxel by voxel (the detector 420 and secondary beam collimator 416 may move dependently from the excitation beam source 412). In some embodiments, one or both of the incident source beam and the exit beam detection may be rastered. In other embodiments, individual point(s) of interest may be selected, in which case, the scanning may not be required.

Relative temporal information may be obtained by measuring two or more points of interest simultaneously, or measuring a point of interest at two or more time points. As an example, using two or more detectors and/or two or more incidental beams, measuring two or more points of interest simultaneously may yield information of the tissue, agent spatial distribution, and/or electron density (or function) at that time point. As another example, measuring spatially distribution of a point of interest at two or more time points may yield the temporal information of how the spatial distribution (and/or electron density) of an agent changes over time. In some embodiments in which more than one excitation beam and more than one corresponding detector are used, the amount of raster scan may be reduced.

In any of the embodiments described herein, a processor may be configured to perform a process (e.g., a reconstruction process) to analyze the acquired data and transform the data to a result in a form appropriate for use in medical or non medical (e.g. industrial, security, etc.) application. Any of the acquired data, information, and results described herein may be stored in a non-transitory for later processing/use, and/or for display on a screen.

Figure 6:
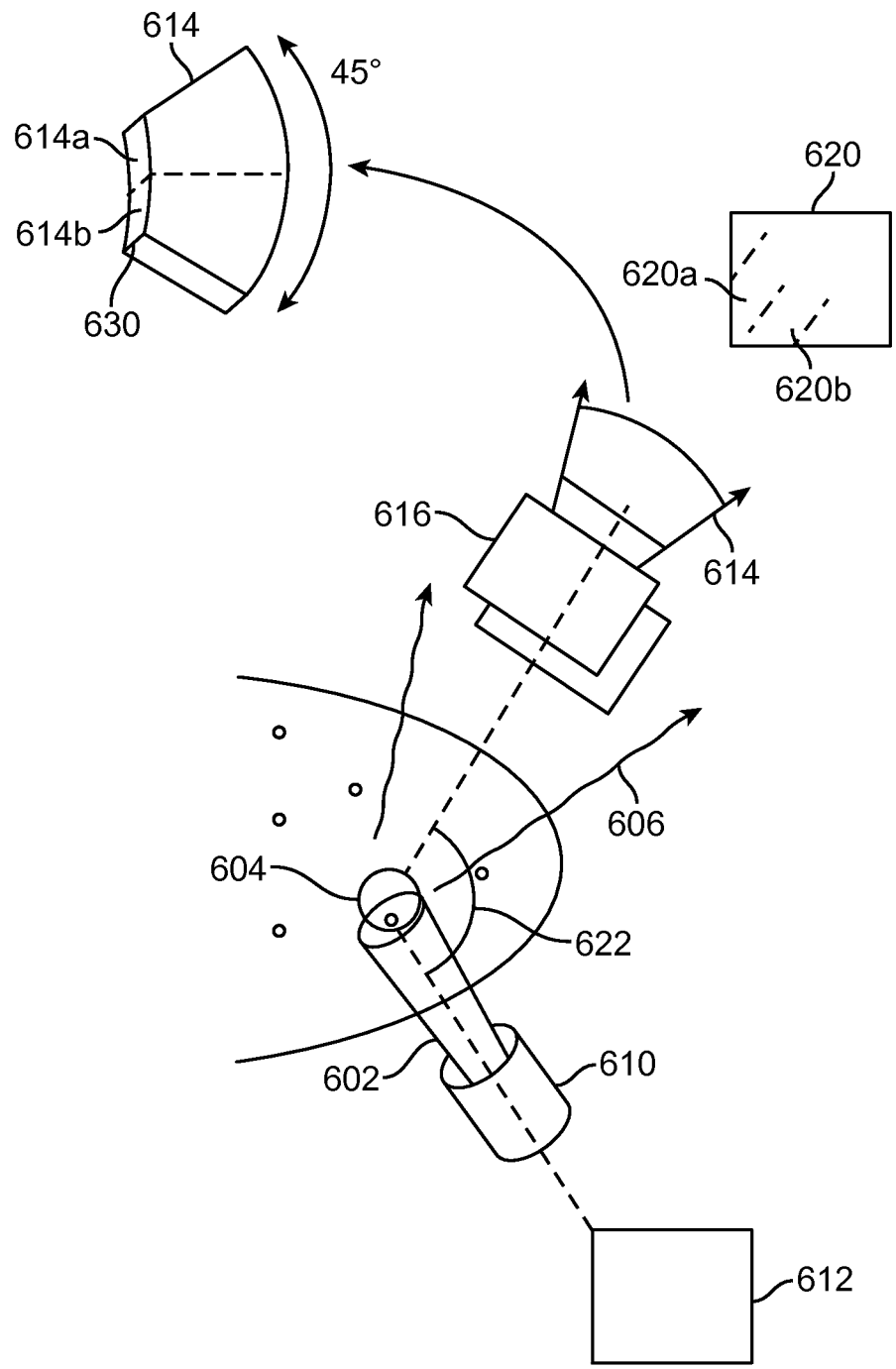
FIG. 6 is a schematic illustration of an example of a pencil beam source as the radiation source and planar secondary beam detection mode in accordance with some embodiments.

In any of the embodiments described herein, the excitation beam 104 may be a pencil beam, and the secondary beam may be a planar beam (excitation pencil beam—secondary planar beam detection mode). FIG. 6 illustrates a detection system that utilizes excitation pencil beam and detected secondary planar beam in accordance with some embodiments. In this embodiment, the excitation beam is emitted from x-ray source 612 (which may be an example of the source 102 of FIG. 1) and collimated by a first collimator 610 (which may be an example of the collimator 106 of FIG. 1) into excitation pencil beam 602. The excitation pencil beam 602 may have monochromatic or multi-chromatic spectral characteristics. The excitation pencil beams' energy and intensity may also be modified through Bragg diffraction, crystal selection, and/or collimation. The secondary beams 606 are generated by interaction of the excitation beam 602 with a voxel 604 of tissue and imaging agent within the target volume. The secondary beams 606 are collimated by a planar collimator 616 (which may be an example of the collimator 114 of FIG. 1), and are received by the detector 620 (which may be an example of the detector 120 of FIG. 1). In the illustrated embodiments, the shape of the secondary planar analysis beam 614 resembles a sector (e.g., a plane figure bound by two radii and the included arc of a circle) having a thickness 630. The thickness of the sector-shaped secondary planar beam 614 is approximately the diameter of the excitation pencil beam 602 and the arc of the sector is 45 degrees. In some embodiments, collimator 616 may be sectioned into multiple ports to produce respective beams 614a, 614b, with detector 620 having respective detector regions 620 a, 620b for sensing the radiation beams 614a, 614b after passing through a subject. Although two beams 614a, 614b are shown, in other embodiments, the number of beams may be more than two. In other embodiments, the shape of the planar beam 614 may have different shapes, and/or different thicknesses, from those described. Also, in other embodiments, the detector 620 may have different configurations.

In the illustrated embodiments, the shape of the voxel is approximately spherical (e.g., radius defined by the diameter of the excitation pencil beam) and defined by a volume which is the intersection of the plane of the excitation pencil beam cross-section and the collimation plane cross-section or ports thereof. This mode may detect the spatial and temporal data of the voxel at a higher sensitivity than the excitation pencil beam—secondary pencil beam detection mode. In some embodiments, with multi collimator ports, multiple voxels may be investigated simultaneously. Also, in some embodiments, a multiport collimator, in combination with a stacked multiple sectors detector, may be used to view individual voxels along the entire length (or a portion) of the incident pencil beam 602, thereby performing a line scan with high sensitivity. To collect volumetric data, raster scanning may be performed. The raster scan can either be a point by point scan (three-dimensional scans of a volume), or line by line scan (two-dimensional line scans of a volume). Use of multiple excitation pencil beams (e.g., multiple radiation sources) and multiple detectors can reduce the raster scan performed.

Figure 6A:
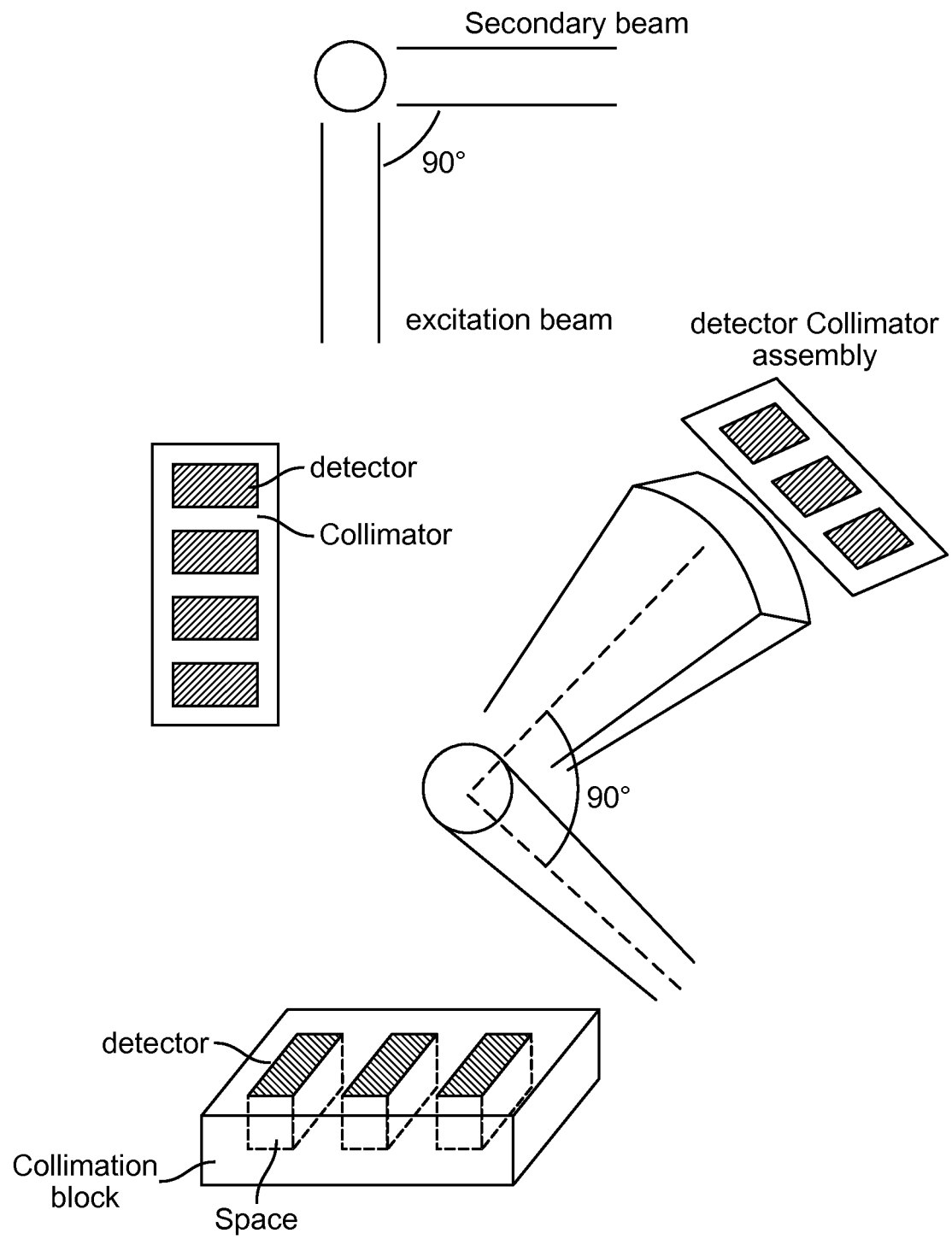
FIG. 6A is an alternative schematic illustration of a pencil beam source as the radiation source and planar secondary beam detection mode, and the planar collimator, in accordance with some embodiments.

The embodiments of FIG. 6 may have different variations. For example, in a configuration where the direction of the excitation pencil beam 602 is perpendicular to the plane of the secondary planar beam 614 (e.g., detector is placed at 90 degree angle relative to the x-ray source 612, shown in FIG. 6A), the data collected by the detector 620 detecting the planar beam 614 is related to the line integral of the interactions along the excitation pencil beam path. In other embodiments, instead of 90°, the detector 620 may be placed at any angle relative to the x-ray source 612. In some cases, the line integral may be used to survey the boundaries of a sub-set volume having high density of imaging agent within the target volume. Also, during an imaging procedure, after the boundaries are surveyed, the imaging system may be reconfigured to operate in a different mode to investigate detail agent distribution in a more restricted volume. For example, in some embodiments, the collimator/detector may be moved closer or further from the target object, thereby changing the size/shape of the observed voxel. In other embodiments, in addition or in the alternative to moving the collimator/detector, the collimator components may be mechanically adjusted to make the ports smaller or larger, e.g. the height 630 may be changed. These are examples of changes in the detection collimation and detector properties. Similar changes may be made in the source collimation and source properties in other embodiments.

In any of the embodiments described herein, a processor may be configured to perform a process (e.g., a reconstruction process) to analyze the acquired data and transform the data to a result in a form appropriate for use in medical or non medical (e.g. industrial, security, etc.) application. Any of the acquired data, information, and results described herein may be stored in a non-transitory for later processing/use, and/or for display on a screen.

In any of the embodiments described herein, the excitation beam 104 may be a planar beam, and the secondary beam may be a pencil beam (excitation planar beam—secondary pencil beam detection mode). In this embodiment, the excitation beam 104 is collimated into excitation planar beam 104. The excitation planar beam 104 may have monochromatic or multi-chromatic spectral characteristics. The excitation planar beams' energy and intensity may also be modified for a particular application through Bragg diffraction, crystal selection, and collimation. The secondary beams 112 are generated by interaction of the excitation planar beam 104 with a voxel of tissue and imaging agent within the target volume. The secondary beams 112 are collimated by a pencil collimator. This detection mode may be used to view individual voxels along the entire length, or a portion of the length, of the secondary beam 112. For an example, the detector 120 may be placed stationary relative to the target volume and the x-ray source 102. The x-ray source 102 may be translated in any direction which moves the intersection point along the axis of beam 112 to collect data of voxels within the target volume that are along the path of the detection beam. For example, in some embodiments, the source 102 may translate in either or both directions that are parallel to the axis of beam 112. The data collected by the detector 120 detecting the secondary beam 112 is related to the line integral of the interactions along the path of the secondary beam 112. In other embodiments, instead of 90°, the detector 120 may be placed at any angle relative to the x-ray source 102. In some embodiments, the system 10 may be reconfigured during an imaging session to a mode to investigate detail agent distribution in a more restricted volume.

Figure 7:
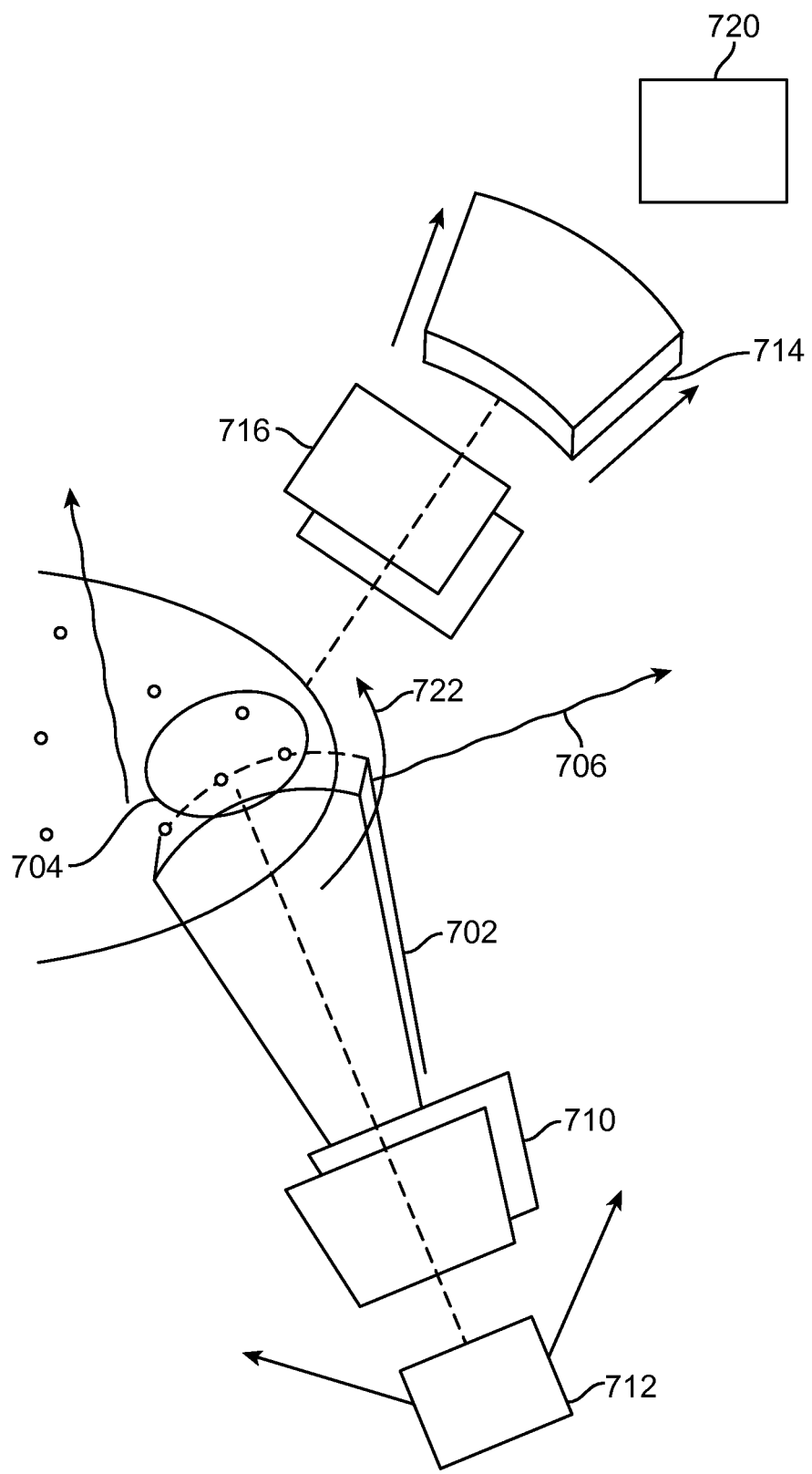
FIG. 7 is a schematic illustration of CT imaging using a planar beam source as the radiation source and planar secondary beam detection mode in accordance with some embodiments.

In any of the embodiments described herein, the excitation beam 104 may be a planar beam, and the secondary beam may also be a planar beam (excitation planar beam—secondary planar beam detection mode). FIG. 7 illustrates a detection system that utilizes excitation planar beam and detected secondary planar beam in accordance with some embodiments. In this embodiment, both excitation beams and secondary beams are each collimated by a planar collimator. In particular, the excitation beam 702 is emitted from x-ray source 712 (which may be an example of the source 102 of FIG. 1) and collimated by a first collimator 710 (which may be an example of the collimator 106 of FIG. 1) into excitation planar beam 702. The excitation planar beam 702 may have monochromatic or multi-chromatic spectral characteristics. The excitation planar beams' energy and intensity may also be optimized through Bragg diffraction, crystal selection, and/or collimation. The secondary beams 706 are generated by interaction of the excitation beam 702 with a voxel 704 of tissue and imaging agent within the target volume. The secondary beams 706 are collimated by a planar collimator 716 (which may be an example of the collimator 114 of FIG. 1), and are received by the detector 720 (which may be an example of the detector 120 of FIG. 1). The data collected by the detector 720 detecting the secondary planar beam 714 is a line integral of the scatter along the path of the excitation beam 702. In other embodiments, multiple beam sources 712 and/or multiple detectors 720 may be used. Mounting multiple excitation beam sources 712 and multiple detectors 720 on a gantry (e.g., a gantry with a rotational axis like that for a CT machine), and collecting data from multiple directions or angles relative to the target volume 704 allows for reconstruction of volumetric image of the radioactive imaging agent distribution within the target volume 704. The reconstruction algorithm would be similar to those used in CT, MRI, and PET.

As describe above, in some embodiments, the source beam may be positioned (e.g., translated) during an examination process. In other embodiments, the source beam may be stationary and the detector beam may be translated. In some embodiments, the movement (e.g., translation) of the source 102 and/or the movement (e.g., translation) of the detector, may be used with a planar fan detection (FIG. 6), with a planar fan source, or with both a planar fan detection and a planar fan source (FIG. 7), to thereby collect data over entire volumes, or sub volumes of the target. In any of the embodiments described herein collimation ports for the detector side and/or collimation port for the source side, may be provided in combination with the movement of the source and/or movement of the detector to further enhance the utility of data collection.

In any of the embodiments described herein, the imaging data received from detecting the secondary beams 112 may be reconstructed into a volumetric image using a technique that is similar to CT reconstruction. In a CT reconstruction, the radiation source configured to deliver a fan beam (or any other beam shape) is rotated to different gantry angles, and image data of a target region are obtained at different gantry angles. The image data are used to determine an integral of data at any given point in the target volume, and a volumetric image is constructed. In some embodiments (involving secondary beam at an angle relative to the incidental beam), to construct a volumetric image, similar technique is used (i.e., obtaining image data from different positions relative to the target region, e.g., at different angles, and using reconstruction algorithm to reconstruct an image). However, the difference is that in a standard CT reconstruction algorithm, it is designed for reading the image data of photonic transmission through the target volume, versus that in the current embodiments, the reconstruction algorithm is configured to correct for difference in photonic energy of the incidental beam at different points along the beam path, as well as degradation/changes of the secondary radiation as it travels through the target volume (post scattering). In particular, standard X-ray CT may be obtained from the measurement of X-ray transmission through an object being imaged where one only needs to determine the ratios of the exit intensity to the entry intensity along every straight line path of X-rays through the imaged object. One has no need to determine how this intensity varies along this straight line path but only the ratios of its initial and final values. On the other hand, in accordance with some embodiments, the object analysis technique described herein measures the exit intensity of X-rays scattered (or of X-ray fluorescence generation) from the straight line path of transmission CT measurements. In some embodiments, to get useful information from such technique, an algorithm may be employed that considers (e.g., determines) how much the incident X-ray intensity is attenuated up to the point at which scattering (or fluorescence generation) occurs, and the decrease in the scattered (or fluorescence) X-ray intensity from the point at which the scattering (or fluorescence) occurs to the point at which the scattered (or fluorescence) X-rays exit the object. In some embodiments, the algorithm may be configured to consider (e.g., determine) two (or more) ratios to obtain useful information from the imaging technique described herein. For example, the first ratio may be ratios of the initial entry intensity to their values at the point of scattering or of fluorescence generation are determined. The second ratio may be ratios of scattered or fluorescence generation intensities to their exit intensities. These two are partial path ratios that are not along the single straight line path with the single ratios required for standard CT.

It should be noted that the algorithm for analyzing the data collected by the imaging device is not limited to the example described, and that different algorithms may be used in different embodiments. By means of non-limiting examples, the algorithm may be a CT data analysis algorithm, a x-ray data analysis algorithm, a MRI data analysis algorithm, a PEP data analysis algorithm, a nuclear spectroscopy data analysis algorithm, or other types of data analysis algorithm, depending on the type of imaging modality being used. In one or more embodiments, the analysis algorithm may be specifically configured for evaluation of functional properties. In some embodiments, the analysis algorithm may be configured based on apparatus design, physics of radiation incident and exiting, and the tissue property (properties) or function (functions) of interest.

In the above embodiments, the excitation beam 104 and the secondary beam 112 have been described as having a "pencil" or planar configuration. In other embodiments, the excitation beam 104 and/or the secondary beam 112 may have different configurations. For example, in other embodiments, one or both of the beams 104, 112 may have a customized cross-sectional shape and size, in which cases; the beam does not have a planar configuration or a pencil-like configuration. In some cases, the shape of the beam may be defined by three dimensional configurations that are extensions of pencil and planar beam shapes. Differential dimensional configurations of excitation and secondary beams 104, 112, and their subsets, can be implemented in varieties of different combinations for medical imaging under different circumstances.

There are many possible configurations to the system 10 and methods described herein. One possible configuration is the choice of the imaging agent, which may be naturally occurring or injected. The considerations in choosing an imaging agent include sufficient contrast, excitation radiation cross section (e.g., the effective diameter of the atom that x-ray is interacting with), and detectable characteristic radiation. Other possible configurations may be achieved by using different configurations for the excitation beam 104, different configurations for the secondary beam 112, and/or different configurations for the detector collimation 106 and/or 114. In some embodiments, the excitation beam 104, the secondary beam 112, and/or the collimator(s) 106, 114 may be configured reduce or minimize background photons from the source 102, so that photons from mainly a defined voxel (with certain location, size, and/or shape), and not the source 102, is used. Other possible configurations may be achieved by using different energy spectrums of the excitation beam 104 and/or different intensities of the excitation beam 104. By choosing a proper energy spectrum of the excitation beam 104 and the proper intensity of the excitation beam 104, the system may provide better data and unique recognition of the imaging agent. For example, a mono-energetic excitation beam with energy characteristics different from the characteristics of the secondary radiation from imaging agent may be desirable in some applications. The radiation source 102 may be generated from a radioactive source, Bragg diffraction from an x-ray tube, or any other type of radiation generator that produces a well collimated beam with a controlled energy spectrum (e.g., mono-energetic beam with one or more energies). Other possible configurations may be achieved by using different detectors with different energy resolutions, or detectors with different detector efficiencies. For example, detector efficiency may be chosen to provide sufficient sensitive and accurate measurements. Other factors to consider while configuring the system may include the consideration of limiting the radiation dose given to a patient in a clinical setting to be within a tolerable level yet produces acceptable imaging results. Other factors to further consider while configuring the system may include broader spectrum radiation or varying different quantum attributes of the incidental radiation energy.

Also, in other embodiments, the detector 120 may have an arc configuration. For example, in some cases, the arc of the detector 120 may partially circumscribe an object under examination, wherein the arc may extend at least 90° circumferentially, or more preferably, at least 180° circumferentially. In other embodiments, the detector 120 may extend 360° circumferentially. In such cases, the detector 120 has a ring configuration with an opening in the middle for accommodating the object under examination.

Figure 8:
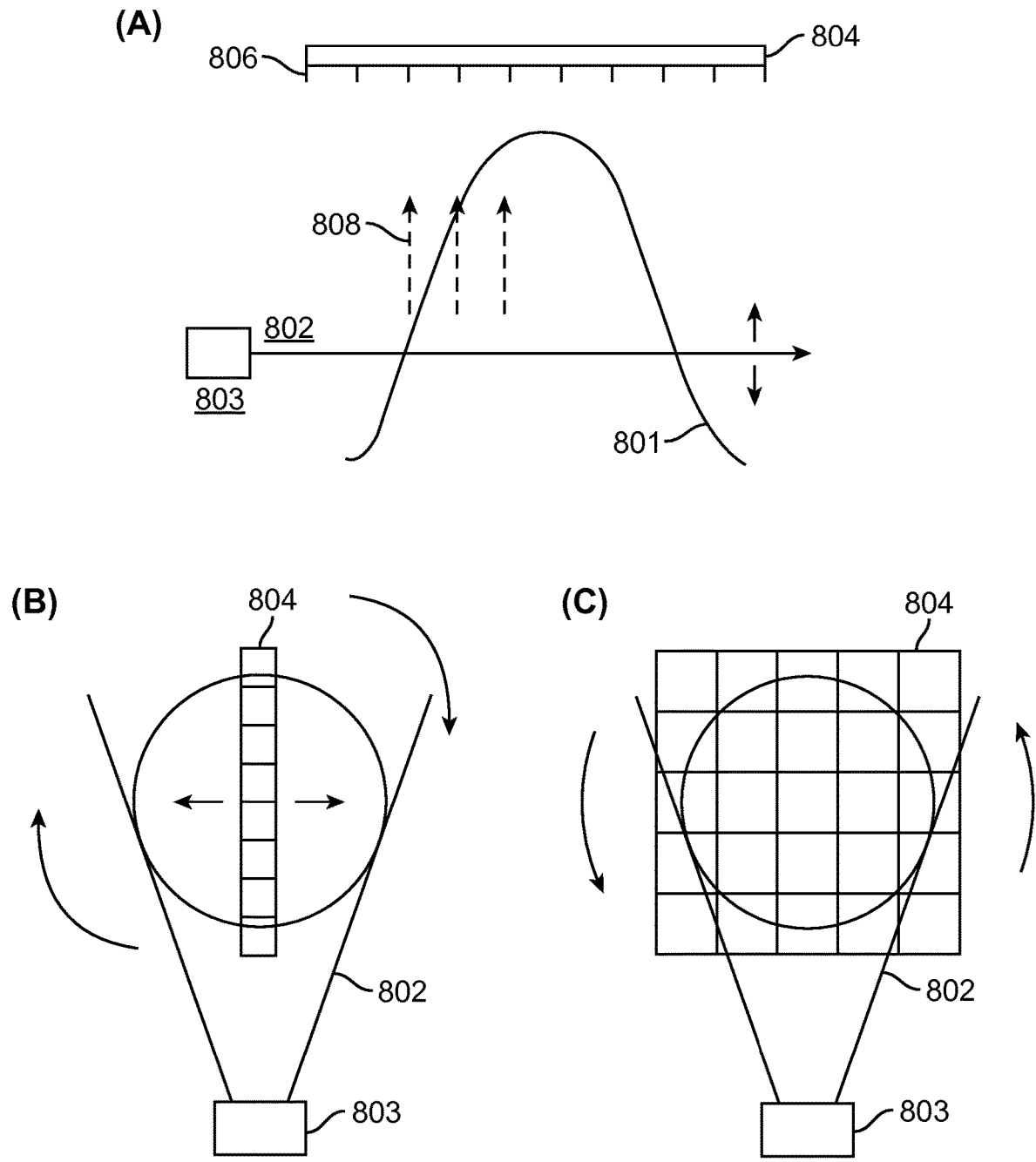
FIG. 8 is a schematic illustration of an example of a planar beam source as the radiation source and planar secondary beam detection mode in accordance with some embodiments.

In some embodiments, the system 10 may be configured to produce CT images in high efficiency. As shown in FIG. 8, an exemplary system is configured to produce 3D CT images of a target volume (e.g., a breast). An x-ray source 803 (which may be an example of the source 102 of FIG. 1) is configured to project toward a target volume 801, an incidental x-ray beam 802 that can be collimated in different shapes. In this exemplary configuration, a beam 802 is planar. The x-ray beam 802 is projected across the target volume 801, producing secondary x-ray 808, the path of which is perpendicular to the path of the x-ray beam 802 (e.g., at a 90° angle to the x-ray source 803). The secondary x-ray 808 is collimated by collimator 806 (which may be an example of the collimator 114 of FIG. 1) and detected by detector 804 (which may be an example of the detector 120 of FIG. 1). The detector 804 detects projection data which is the integrated scattering data that is along the path of secondary x-ray 808 through the portion of the target volume 801 that is between the path of the incidental beam 802 and the detector 804. In order to receive more projection data to reconstruct 3D CT image, the x-ray source 803 may move toward the detector 804 (See movement arrow pointing towards the detector 804 in FIG. 8 (A)). The detector 804 can be a small strip detector (See FIG. 8 (B)), or a large area detector (See FIG. 8(C)). In FIG. 8 (B), where a strip detector is used, the detector 804 may be moved left or right as shown in the figure. Also, the x-ray source 803 may rotate partially or completely (e.g., 180°-360°) around the target volume 801. The x-ray source 803 may also move toward or away from the detector 804, as discussed. Alternatively, the strip detector 804 may be oriented 90° from that shown in the figure, and be moved up and down (i.e., in a direction that is parallel to the axis of the beam 802). In FIG. 8(C), where an area detector 804 is used, the x-ray source 803 may rotate partially or completely (e.g., 180°-360°) around the target volume 801, and/or may move toward or away from the detector 804. The collected projection data can then be used to reconstruct a 3D image of the target volume 801. An algorithm may be employed to reconstruct the 3D image. In some embodiments, the algorithm may be configured to correct for difference in photonic energy of the incidental beam at different points along the beam path, as well as degradation/changes of the secondary radiation has it travels through the target volume (post scattering). By means of non-limiting examples, the algorithm may be a CT data analysis algorithm, a x-ray data analysis algorithm, a MRI data analysis algorithm, a PEP data analysis algorithm, a nuclear spectroscopy data analysis algorithm, or other types of data analysis algorithm, depending on the type of imaging modality being used.

Figure 9:
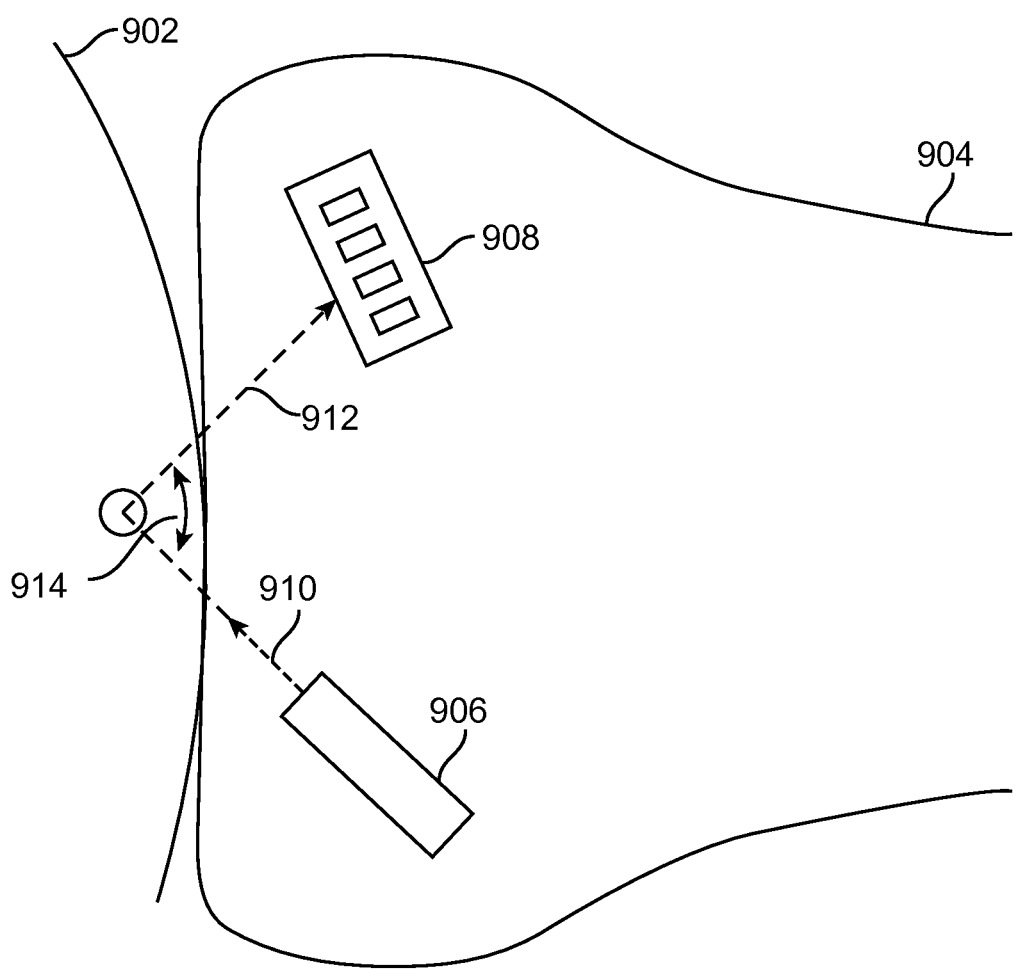
FIG. 9 is a schematic illustration of an apparatus configuration in accordance with some embodiments.

In other embodiments, an apparatus may be provided that includes both the x-ray source and the detector in the same probe to form a compact x-ray imaging device, similar to an ultrasound probe wherein the ultrasound emitter and the detector are included within the same probe housing. As shown in FIG. 9, the radiation source 906 and detector 908 are placed within a probe 904, which is configured for scanning a target volume 902. The radiation source 906 and the detector 908 can be placed at an angle 914 relative to each other. The angle 914 is approximately 90° (e.g., 90°±10°). In other embodiments, the angle 914 may be different from 90°, and may be a value that is anywhere between 0° and 180° and more preferably between 45° and 135°). During use, the excitation radiation beam 910 is emitted towards the target volume 902, and secondary radiation beam 912 is detected by detector 908. Signals from the detector 908 may be used to obtain information about the target volume 902, as similarly discussed herein.

As described in some of the above embodiments, the source collimator may be configured to provide a plurality of ports to create multiple source beams, and/or the detector collimator may be configured to provide a plurality of ports to create multiple secondary (analysis) beams. It should be noted that each port (at the source collimator or the detector collimator) may be configured (e.g., by operating the collimator) to produce a beam having any desired cross sectional shape, which may or may not vary in the longitudinal direction. In some embodiments, the beams (e.g., pencil beams) from the ports (e.g., source collimator ports, or detector collimator ports) may or may not overlap in the longitudinal direction. Also, in some embodiments, the beams (e.g., pencil beams) from the ports may be essentially parallel or they may come to a focus at some arbitrary longitudinal position. In some cases, there may be more than one focal point from different beams. In any of the embodiments described herein, each port may be configured to provide an arbitrary cross sectional cone, focusing at infinity or at certain longitudinal position. In different embodiments, the source supplying radiation to the ports may have different properties, such as different central quantum energy or spectra, different intensity, etc. Also, in different embodiments, the detector for receiving beams from different ports may have different properties, such as sensitivity to intensity, sensitivity to secondary quanta energy, etc.

Also, although several examples of the examination system have been described in different embodiments above, it should be noted that the system for examination subject is not limited to the examples described, and that the system may have different configurations in different embodiments. By means of non-limiting examples, possible configurations for the examination system may include the following in different embodiments:

(A) One or more beam sources and one or more detectors;
(B) A pencil beam source configured to provide a pencil beam, and a detector collimator with a single port configured to provide a secondary beam for detection by the detector;
(C) A pencil beam source configured to provide a pencil beam, and a detector collimator with a multiple ports configured to provide multiple secondary beams (e.g., fan beams, focused cone beams, or unfocused cone beams) for detection by the detector (for example, like that shown in FIG. 10A);
(D) A source collimator with a single port configured to provide a beam (e.g., fan beam, focused cone beam, or unfocused cone beam), and a detector collimator configured to provide a pencil secondary beam for detection by the detector;
(E) A source collimator with a multiple ports configured to provide multiple beams (e.g., fan beams, focused cone beams, or unfocused cone beams), and a detector collimator configured to provide a pencil secondary beam for detection by the detector;
(F) A source collimator with a single port configured to provide a beam (e.g., fan beam, focused cone beam, or unfocused cone beam), and a detector collimator with a single port configured to provide a secondary beam (e.g., fan beam, focused cone beam, or unfocused cone beam) for detection by the detector;
(G) A source collimator with a single port configured to provide a beam (e.g., fan beam, focused cone beam, or unfocused cone beam), and a detector collimator with multiple ports configured to provide multiple secondary beams (e.g., fan beams, focused cone beams, or unfocused cone beams) for detection by the detector;
(H) A source collimator with multiple ports configured to provide multiple beams (e.g., fan beams, focused cone beams, or unfocused cone beams), and a detector collimator with a single port configured to provide a single secondary beam (e.g., fan beam, focused cone beam, or unfocused cone beam) for detection by the detector; or
(I) A source collimator with multiple ports configured to provide multiple beams (e.g., fan beams, focused cone beams, or unfocused cone beams), and a detector collimator with multiple ports configured to provide multiple secondary beams (e.g., fan beams, focused cone beams, or unfocused cone beams) for detection by the detector.

In any of the embodiments described above, the source may provide beam(s) that is focused, and the secondary beam(s) may be unfocused. In other embodiments, the source may provide beam(s) that is unfocused, and the secondary beam(s) may be focused. In still other embodiments, the source may provide beam(s) that is focused, and the secondary beam(s) may also be focused. In further embodiments, the source may provide beam(s) that is unfocused, and the secondary beam(s) may also be unfocused. Also, in any of the embodiments described herein, any of the beams (source beam or secondary beam) may be a partial beam (e.g., a partial fan beam) or a full beam (e.g., a full fan beam). A full beam is a beam that is wide enough to cover the entire width of an object of interest, and a partial beam does not.

The various configurations of source and detection described herein may produce information about local points, points along a line, points on a surface, or points in a volume. Such information may be obtained from the data collected by data processing. In some embodiments, this processing may involve CT like reconstruction. In other embodiments, there is no requirement for CT like reconstruction. In either case, algorithms may be provided to process and/or interpret the data to present the information of interest. Also, in any of the embodiments described herein, the data collected using the detector(s) may be processed to produce information of interest such as physical information, and/or functional information. The physical information and/or functional information may be in a one, two, or three-dimensional space domain and/or in a temporal domain. In some embodiments, if the physical information or functional information are generated in a three-dimensional space domain and over time, then such information may be called 4d physical medical characterization or 4d functional medical characterization.

Figure 10A:
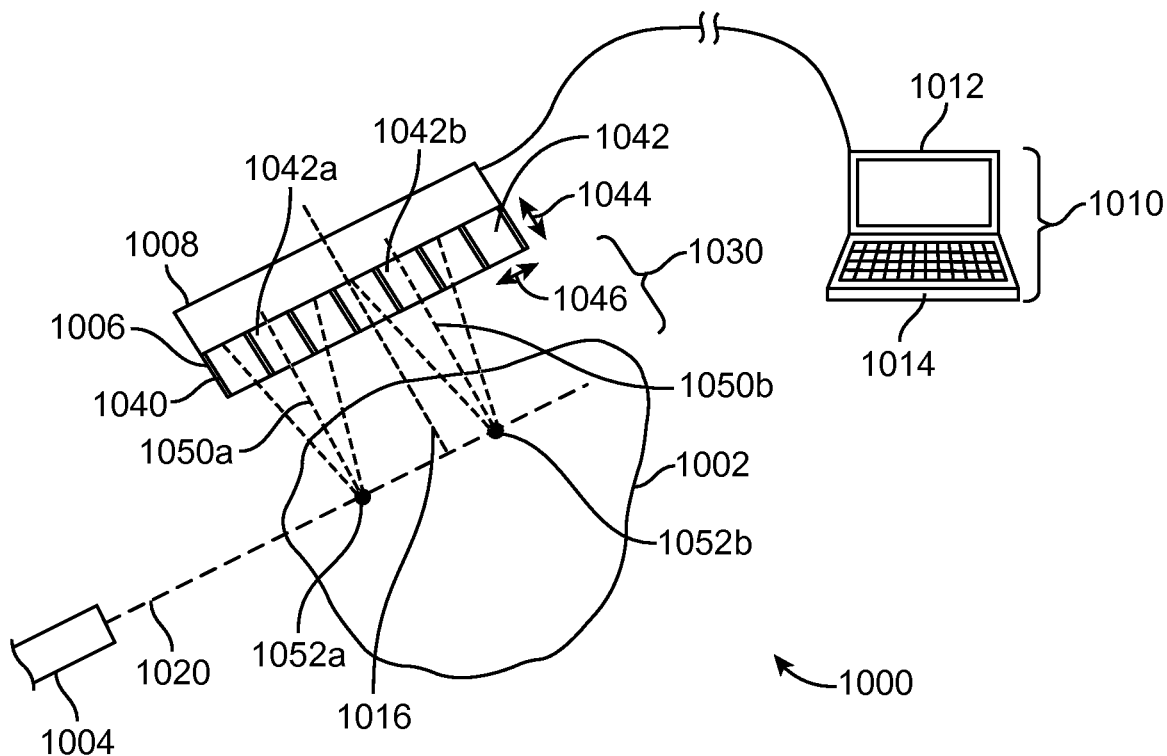
FIGS. 10A and 10B illustrate an apparatus for examining a target in accordance with some embodiments.

FIG. 10A illustrates an apparatus 1000 for examining a target 1002 in accordance with some embodiments, the apparatus 1000 includes a radiation source 1004, a collimation device 1006, a detector 1008, and a user interface 1010. The user interface 1010 includes a screen 1012 for presenting information to a user, and an input device 1014 for allowing the user to input information. The radiation source 1004 may be configured to provide x-ray energy having a value that may range from 30 keV to 150 keV. In other embodiments, the radiation source 1004 may be configured to provide x-ray energy having other energy levels. Also, in some embodiments, the radiation source 1004 may include a x-ray tube with a single crystal for providing diffraction to create a beam with mono-energy (e.g., energy spectrum having a peak). In addition, in some embodiments, the radiation source 1004 may include a radioactive source, such as Am 241, which produces a high purity 59.9 keV x-ray (e.g., a x-ray with defined spectrum having a peak at 59.9 keV).

As shown in the figure, the collimation device 1006 and the detector 1008 are located at an angle 1016 less than 180 degrees relative to a beam path of the first beam 1020. In the illustrated embodiments, the detector 1008 is a x-ray quantum energy sensitive detector. The detector 1008 may be a single crystal HgI detector in some embodiments. In other embodiments, the detector 1008 may be a CdTe detector. In further embodiments, the detector 1008 may include other materials/composition.

In the illustrated embodiments, the radiation source 1004 is configured to deliver a first beam 1020 (e.g., a first x-ray beam) towards the target 1002 for examining the target 1002. The first beam 1020 interacts with the target 1002 to produce second beam 1030. The second beam 1030 is the result of interaction of the incident beam 1020 with agents in the target 1002, wherein the agents may be a variety of substances (e.g., iodine, barium, tissue, electrons, etc.). In some embodiments, the examination of the target 1002 is based on monochromatic spectral characteristics of the excitation. In other embodiments, the examination of the target 1002 may be based on other spectral characteristics of the excitation.

In the illustrated embodiments, the first beam 1020 is a pencil beam, which interacts with different parts 1040a, 1040b of the target 1002 along a line. As used in this specification, the term "pencil beam" should not be limited to a beam having a narrow diameter, and may refer to a beam having any cross sectional dimension. For example, in some embodiments, a pencil beam may have a cross sectional width that is wide enough to cover an entire target 1002 that is desired to be examined. In other embodiments, a pencil beam may have a cross sectional width that is smaller than the target 1002, in which case, the pencil beam is configured to interact with a subset of the target 1002. Although two points/regions 1040a, 1040b are shown, it should be understood that the first beam 1020 will interact with more than two points/regions along the beam axis.

As shown in the illustrated embodiments, the second beam 1030 is received by the collimation device 1006, which collimates the second beam 1030 before the second beam 1030 reaches the detector 1008. In particular, the collimation device 1006 includes walls 1040 that define a plurality of openings 1042 for allowing the second beam 1030 to exit therethrough. Each opening 1042 has a depth 1044 measured in a direction perpendicular to a plane of the detector 1008 that is longer than a width 1046 of the opening 1042. Such configuration provides more accurate collimation for the second beam 1030. In other embodiments, the depth 1044 may be shorter than the width 1046, or the same length as the width 1046. Also, in the illustrated embodiments, each wall 1040 has a plane that is perpendicular (e.g., 90 degrees±2 degrees) to a plane of the detector 1008. In other embodiments, each wall 1040 may form a non-perpendicular angle relative to the plane of the detector 1008.

As shown in FIG. 10A, the second beam 1030 includes a first portion 1050a resulted from an interaction of the first beam 1020 with a first part 1052a of the target 1002, and a second portion 1050b resulted from an interaction of the first beam 1020 with a second part 1052b of the target 1002. The first portion 1050a of the second beam 1030 is collimated by the device 1006 so that a part of it that travels substantially perpendicular towards the device 1006 will go through the device 1006 (e.g., through the opening 1042a), with the remaining part (e.g., the diverging part) being blocked by the walls 1040 of the device 1006. Similarly, the second portion 1050b of the second beam 1030 is collimated by the device 1006 so that a part of it that travels substantially perpendicular towards the device 1006 will go through the device 1006 (e.g., through the opening 1042b), with the remaining part (e.g., the diverging part) being blocked by the walls 1040 of the device 1006.

Figure 10B:
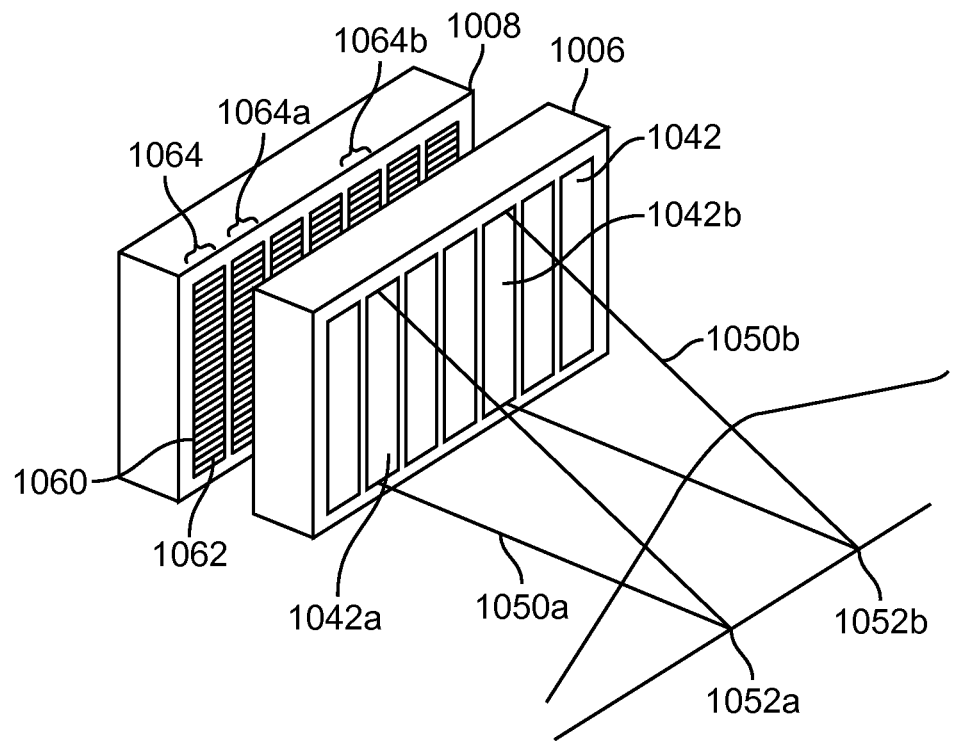

As shown in FIG. 10B, the detector 1008 includes a plurality of detector elements 1060 that are aligned with respective openings 1042 of the collimation device 1006. Each detector element 1060 includes six sub-detector elements (channels) 1062. In other embodiments, each detector element 1060 may include more than six channels, or fewer than six channels. The detector elements 1060 are arranged in a plurality of columns, which each column 1064 having four detector elements 1060. In other embodiments, each column 1064 may have more than four detector elements 1060 or fewer than four detector elements 1060.

Following the above example, after the first portion 1050a of the second beam 1030 has been collimated by the device 1006, the first portion 1050a of the second beam 1030 exits from the other side of the device 1006 to reach the corresponding detector elements 1060 that are aligned with the opening 1042a. Similarly, after the second portion 1050b of the second beam 1030 has been collimated by the device 1006, the second portion 1050b of the second beam 1030 exits from the other side of the device 1006 to reach the corresponding detector elements 1060 that are aligned with the opening 1042b. Because the openings 1042a, 1042b have an elongated configuration, the portions 1050a, 1050b of the second beam 1030 exiting the collimation device 1006 will have a fan-like, or planar configuration. In some embodiments, the collimator and detector are physically attached to each other. In other embodiments, there may be a space between the collimator and the detector.

Figure 10C:
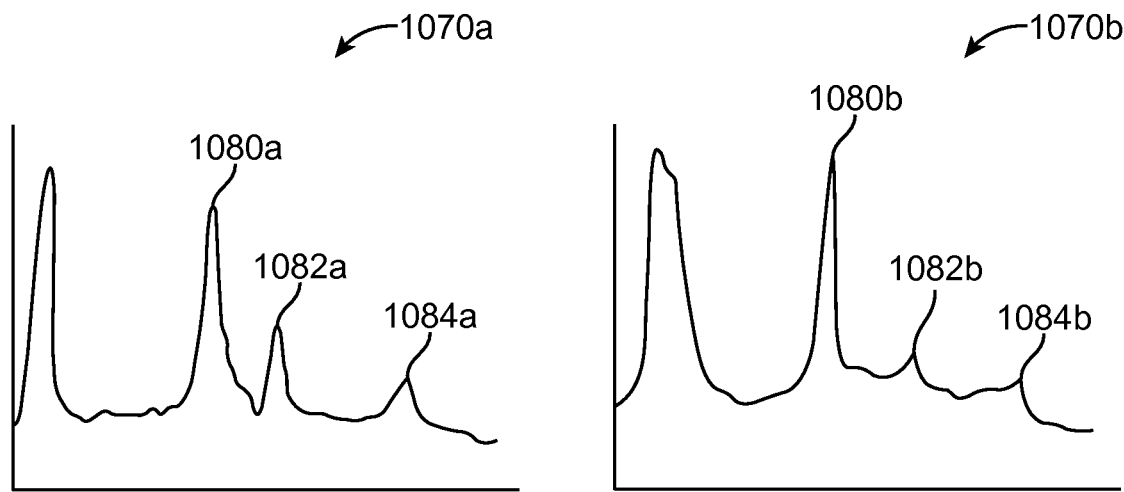
FIG. 10C illustrates energy spectrum data obtained using the apparatus of FIGS. 10A and 10B in accordance with some embodiments.

In the illustrated embodiments, the detector 1008 is an energy spectrum counting detector. Thus, each detector element 1060 is configured to detect counts corresponding to different energy levels. FIG. 10C illustrates a first energy spectrum 1070a provided by the column 1064a of detector elements 1062 that is aligned with the opening 1042a, and a second energy spectrum 1070b provided by the column 1064b of detector elements 1062 that is aligned with the opening 1042b. The first energy spectrum 1070a includes a k-Alpha peak 1080a, a k-Beta peak 1082a, and a Compton scatter peak 1084a. Similarly, the second energy spectrum 1070b includes a k-Alpha peak 1080b, a k-Beta peak 1082b, and a Compton scatter peak 1084b. The energy spectrums 1070a, 1070b may be displayed on the screen 1012 for allowing a user to view the information. Also, in some embodiments, the energy spectrums 1070a, 1070b may be stored in a non-transitory medium for later processing.

As illustrated in the above embodiments, the elongated configuration of each opening 1042 is advantageous because it allows more detectors 1062 to detect radiation coming from a part 1052 of the target 1002. This in turn allows the detector 1008 to obtain the energy spectrums 1070 more efficiently (because multiple detector elements 1062 in each column 1064 participate in the energy count detection for creating each energy spectrum 1070).

Although only two parts 1052a, 1052b of the target 1002 are illustrated, and two corresponding energy spectrums 1070a, 1070b are described, it should be understood that the target 1002 may have more than two parts 1052, and that in other embodiments, the detector 1008 may provide more than two energy spectrums 1070 that corresponding to different parts of the target 1002.

In some embodiments, the user interface 1010 may include a processing unit configured to process information from the energy spectrums 1070. For example, in some embodiments, the processing unit may be configured to determine a density of a part of the target 1002, or a parameter that correlates with a density of the part of the target 1002. In some embodiments, the target may be tissue that contains iodine. In such cases, the k-Alpha and k-Beta peaks in the spectrum 1070 have respective intensities that are proportional to the iodine density at a nodule in the target 1002. Also, the spectrum 1070 will include a peak due to Compton scatter by electrons, with intensity that is proportional to the electron density of the nodule being examined. Thus, in some embodiments, the intensity of the x-ray quantum at the iodine k-alpha-1 and iodine k-beta 1 energy may be used as a measure of the iodine density at the voxel being examined. Also, because the Compton scatter peak intensity is proportional to electron density of a part (e.g., a nodule) of the tissue, the Compton scatter peak may be used to determine density of the tissue, or to determine a parameter that correlates with the density of the tissue. In such cases, the intensity of the x-ray quantum at the Compton scatter energy may be used as a measure of the electron density at the voxel being examined.

Since generally the iodine content of the voxel is very small, the electron density is very independent of the iodine density. Thus, in some embodiments, the ratio of iodine K energy to Compton scatter energy may be used as a measure of the relative density of iodine in the voxel. For example, in some embodiments, the processing unit may be configured to calculate a ratio V=k-Alpha peak value/Compton scatter peak value for each of the energy spectrums 1070. The ratio V may be used to correlate with a volume of an agent that is present in the target 1002 being examined. In some embodiments, the ratio(s) V may be displayed on the screen 1012 for allowing a user to view the information. Also, in other embodiments, the ratio(s) V may be stored in a non-transitory medium for future processing. Also, in some embodiments, through system calibration, the absolute value of the iodine density (e.g., concentration in a given tissue volume) may be determined.

As discussed in the above embodiments, the interaction of the radiation with material in the target volume may be characterized by k-Alpha 1 decay from Iodine, and/or Compton scatter from electrons. However, in other embodiments, other k-Alpha value(s) may be used. For example, in other embodiments, the interaction characterization may include one or more ratios calculated using any of k-Alpha 1 decay from Iodine, k-Alpha 2 decay from Iodine, k-Alpha n decay from Iodine, k-Alpha 1 decay from gold, k-Alpha n decay from gold, and k-Alpha n decay from any of other contrast agents. Also, in the above embodiments, Compton scatter is from electrons at 90 degrees. In other embodiments, Compton scatter may be from electrons at 45 degrees, or at any of other angles. Thus, as used in this specification, the term k-Alpha may refer to one or more of k-Alpha-1, k-Alpha-2, . . . k-Alpha-n. Also, as used in this specification, the term "Compton scatter" may refer to Compton scatter at any given angle.

In some embodiments, at the crossing point/region of the incident source beam and the detection beam, a volume of interest may be defined. This may be a small voxel of tissue with irregular shape. In some cases, for two circular beams, the volume of interest may fit inside a sphere with radius of one to ten mm. The measurement of radiation by the detector is essentially all from Compton scatter interactions with the electrons in the volume of interest or photo absorption interactions with the contrast agent (e.g., iodine) in the volume of interest. Near the voxel of tissue, there may also be some radiation effect due to photo absorption interactions with tissue elements, but this has low quantum energy. This radiation is primarily filtered from detection by attenuation. Any of the above described radiation reaching the detector may be distinguished by the energy sensitivity of the detector.

In some embodiments, because the quantum energy of the various types of interaction differ, observed intensities may be labeled as to the type of interaction, $I_{Compton}$, $I_{K-alphaa}$, $I_{K-alph2}$, $I_{K-betaa}$, $I_{K-beta}$, $I_{etc.}$. The unit for each "I" is counts per sec. To a high degree of linearity, the $I_{Compton}$ is proportional to the number of electrons in the volume of interest. Also, assuming the only contrast agent is Iodine, each of the $I_{K_-}$ is proportional to the number of Iodine atoms in the volume of interest. The electron density and the volume of interest do not significantly change with the presence or absence of contrast agent and may be evaluated. In some embodiments, the proportionality associated with each of the $I_k$ (e.g., $I_{K\text{-}alphaa}$, $I_{K\text{-}alph2}$, $I_{K\text{-}betaa}$, $I_{K\text{-}beta}$ etc.) may be represented by a proportionality constant. The proportionality constants associated with $I_{xxx}$ intensities may be evaluated by system calibration and analytic evaluation using tabulated information such as cross section values. In some embodiments, the number of contrast agent atoms in the volume of interest may be determined by taking the product of a constant (which may separately evaluated as discussed) and a sum of one or more $I_K$ divided by $I_{Compton}$. Each count in an $I_k$ may be due to interaction with one contrast agent (e.g., Iodine) atom, and thus the total number of contrast agent atoms is the sum of these counts. In some cases, if each of the $I_K$ is individually used, the result for the number of contrast agent atoms calculated using each $I_k$ should be the same (i.e., $k_1 I_{k1}/I_{Compton} = k_2 I_{k2}/I_{Compton}$, etc.). This may be used as a check of proportionality constants or as a way to assist in system calibration. In other embodiments, by observing the time variation of the $I_{xxx}$ (e.g., how the intensity $I_{xxx}$ changes as a function of time), various rates may be evaluated. By means of non-limiting examples, such rate may be any of substance build up and clearing, motion of nodules in and out of the volume of interest, velocity of this motion, growth rate of leakage and micro vascular, etc.

In other embodiments, if one is interested in looking at the ratio of $I_k$ (or two groups of $I_k$, where each group may contain several peaks at more or less the same energy), then the processor may calculate the ratio of the sums of counts in each group.

In some embodiments, a maximum number of contrast agent atoms in the volume of interest under certain conditions (e.g., under fixed conditions by keeping certain injection parameters constant; parameters such as an amount of contrast, location(s) of where it is injected, rate of injection, composition of the agent, etc.) may be determined. The maximum number of contrast atoms may be used to correlate with cancer size and/or growth. In some embodiments, the value of the maximum number of contrast atoms may be used to determine an increase in Hounsfield units (HU). in a volume of interest. Also, a correlation between the increase in HU due to contrast in a volume of interest and cancer (e.g., size and/or growth rate) may be established. Accordingly, the maximum number of contrast atoms in the volume of interest may be used to determine cancer characteristics (e.g., size and/or growth rate) based on the correlation.

Also, in some embodiments, by making sequence of two or more measurements, for example, at intervals two or three days apart, the growth rate of contrast agent in a voxel of tissue may be determined. The growth rate of a nodule of possibly cancerous tissue is of significant medical interest. In one approach, the maximum number of contrast atoms in the volume of interest may be used at each point in the sequence to determine the HU as a function of time, and relate this to cancer size and/or growth rate. The contrast will stay in the patient body for a period of time and will eventually exit the body through a natural process. While in the body, the contrast will travel with blood. Since a tumor may have an increase in vascular activity (e.g., increase in blood vessel growth), the location of tumor may have relatively more contrast atoms.

In other embodiments, a parameter calculated as the ratio of two $I_K$ (for example $I_{K\text{-}alpha1}/I_{K\text{-}alpha2}$) may be used for medical applications. The $I_{K\text{-}alpha1}$ is influenced by the local environment of a contrast atom. For example, the environment may be the molecular structure of cancer tissue, which is different from non-cancerous tissue. Thus, the ratio calculated using $I_{K\text{-}alpha}$ may be used as a measure of important environmental conditions, such as cancerous condition. In other embodiments, a parameter that relates to changes in the average quantum energy of photo decay due to environment may be measured. Such parameter (which may be a change in the average quantum energy of photo decay) may be used to determine tissue condition. The average quanta energy for k decay of an excited free contrast atom is known. For bound contrast agent atoms, there are small deviations from the free atom value due to the environment. In some embodiments, a very energy sensitive detector may be used to detect environmental differences.

In the above embodiments, the ratio V is calculated as a ratio of peaks. In other embodiments, the ratio V may be calculated as ratio of the areas under respective peaks (e.g., the bell shape peaks) in the energy spectrum 1070. The observed area under the bell shaped curve is related to many quantities of interest for clinical and also non clinical application. These quantities of interest include number and density of electrons, number and density of iodine atoms, rate of change of electrons, and rate of change of iodine atoms. In some cases, the area under a peak may be representative of the intensity of radiation characterized by, for example, its mean quantum energy, at the detector due to scatter interactions within a volume (voxel) of material under investigation.

In other embodiments, the processing unit may be configured to calculate a ratio E=k-Alpha peak value/k-Beta peak value for each of the energy spectrums 1070. The ratio E depends on the environment in which the agent is located. Thus, the ratio E may be used to correlate with characteristic(s) of the target 1002. In some embodiments, the ratio(s) E may be displayed on the screen 1012 for allowing a user to view the information. Also, in other embodiments, the ratio(s) E may be stored in a non-transitory medium for future processing.

Also, the central energy value of the iodine (or another agent) k-alpha-1, and the central energy value of iodine (or another agent) k-beta-1 depend on the atomic environment. Thus, in other embodiments, the central energy values of the k-alpha and k-beta peaks may be used to correlate with characteristic(s) of the target 1002.

In further embodiments, the intensity ratio E and the central energy positions of the k-Alpha peak and the k-Beta peak may be used by the processing unit to differentiate environment at the target 1002, and evaluate pathology of cells and tissue at the target 1002.

It should be noted that k-alpha has a sub structure. An excited atom is an atom where an electron has been removed from an inner shell by e.g. an incoming x-ray. K-alpha radiation results when an electron from an outer shell of an excited atom "falls" to its empty inner shell. The shells may be quantized (numbered), such as, "1" for the inner shell, and "66" for the last outer shell, with each shell having an energy value. When an electron falls from outer shell (e.g., shell #60) to an inner shell (e.g., shell #1), the energy difference between the two shells involved comes out as x-ray, e.g., k-alpha x-ray. In some cases, the difference in energy level between shell #1 and shell #2 is small, and so an electron falling from shell #60 to shell #1, and an electron falling from shell #60 to shell #2, yield x-rays with nearly the same energy. In some cases, the term k-alpha may refer to a group of transition between shells where the energy differences are nearly the same. Each transition in this k-alpha group has a transition decay energy value. Another decay property of each transition is the decay probability for the transition. An excited atom can have its empty shell filled by an electron from various outer shells, wherein each of these is a possible transition and has a probability of occurring. Thus each transition in the k-alpha group has a transition decay probability value. As used here, the term "sub structure" of k-alpha refers to the fact that each transition in the k-alpha group has its own unique decay energy and/or probability. With high energy and intensity resolution, the transition energy and probabilities for each of the transitions in a group may be resolved to allow more detailed examination to be performed. For example, in some embodiments, by analyzing the energy and probabilities of substructure transitions (e.g. using ratios calculated by a processor), more detail information may be obtained.

Also, in some embodiments, the detector 1008 may be configured to repetitively detect energy counts over time to thereby provide a sequence of energy spectrums 1070 over time. The data from the sequence of energy spectrums 1070 may then be analyzed by the processing unit to determine temporal information for the target 1002 being examined. In some embodiments, the system may perform measurement to high accuracy (e.g., within 1%), and the time required for this measurement is short (e.g., one sec or less). Thus, in some embodiments, the energy spectrums 1070 may be processed to determine examination data representing fluid buildup, fluid retention, fluid wash out, rate of fluid buildup, rate of fluid wash out, or combination of the foregoing, in essentially real time. This is possible because within a voxel that is being examined, there are different types of materials, such as electrons, nuclei, atoms, etc. For example, if the tissue being examined includes iodine, then the analysis may involve examining number of electrons and number of iodine atoms in the voxel. At any given time, there will be some number of electrons and some number of iodine atoms. Also, the number of electrons and iodine atoms may be changing with time. Since the measurement may take some duration of time, the resulting measurement is an average measurement. In some embodiments, through measurement and analysis of spectra taken at different times, information about material presents, retention, washout, rate of buildup, rate of washout, and related biophysical function may be determined. In one implementation, any of the above information may be determined by spectrum analysis techniques.

In other embodiments, the measurement and analysis of spectra taken at different times may involve the processing unit examining different parameters over time. For example, in some embodiments, the ratio E, the ratio V, or other parameter(s) may be examined by the processing unit over time to see how the parameter(s) changes, thereby allowing information about material presents, retention, washout, rate of buildup, rate of washout, and related biophysical function to be determined.

Also, in some embodiments, examination data from numerous voxel locations may be associated with each other to determine functional information, such as blood flow. For example, in some embodiments, the processing unit may obtain examination data for two (or more) voxel locations (which might be measured simultaneously with two pencil beams and a pencil detector, or one pencil beam and two pencil detectors in some embodiments), and then process the data to investigate inter relationships between the two (or more) voxel locations, such as blood flow between the two (or more) voxel locations.

In still further embodiments, the target 1002 may include two agents with different k-Alpha and k-Beta energies. By means of non-limiting examples, one agent could be iodine, and the other agent could be barium. The use of multiple agents in the target 1002 may allow additional pathology and functional information to be obtained. For example, if the absorption or attachment of two agents is different due to some characteristic of the tissue at the target 1002, the extent, pathology, or function of this tissue characteristic for the tissue in the voxel may be ascertained from the density and time behavior of the two agents k-quanta. By considering the k-Alpha/k-Beta ratios and central energies for the two agent environmental surrounding, information may be obtained. In some embodiments, the apparatus 1000 may perform time dependent measurement of such pathology and functional information to high accuracy (e.g., within 1%) in short time (e.g., one second or less). Thus, changes in build up, retention, wash out rate, etc. for the two agents may be measured in essentially real time.

It should be noted that the agent(s) that may be included in the target 1002 is not limited to the examples discussed, and that any agent(s) may be used. For example, the agent may be radioactive, or non-radioactive. In some embodiments, the agent may be a naturally occurring element (e.g., element with relatively high Z value). In other embodiments, the agent may be an element attached to some carrier. In further embodiments, the agent may be an injectable element, including but not limited to contrast, micro spheres, a biological material, etc. In still further embodiments, the agent may be contained inside a container. The container may include nanoparticles or lipid bilayer based structures such as liposomes, which may depend on (e.g., interact with) some internal or external stimulant. The external stimulant may be radiation which cracks the container, or may be ultra sound. In other embodiments, the container may include a biological material which is pH or temperature sensitive and thus, allows for pH or temperature dependent opening of the container and release of the agent(s) in a desired area, including but not limited to areas of malignancies or inflammation. In some embodiments, the agent may be used to facilitate pathologic measurements.

Also, in one or more embodiments described herein, the processing unit may use signals from the detector 1008 to construct a model of the target 1002. The model may represent functional and/or temporal characteristics of the target 1002. In some embodiments, the model may be a two dimensional model. In other embodiments, if a volume (instead of a line or a plane) of the target 1002 is scanned, the model created by the processing unit may be a three dimensional model.

Figure 10D:
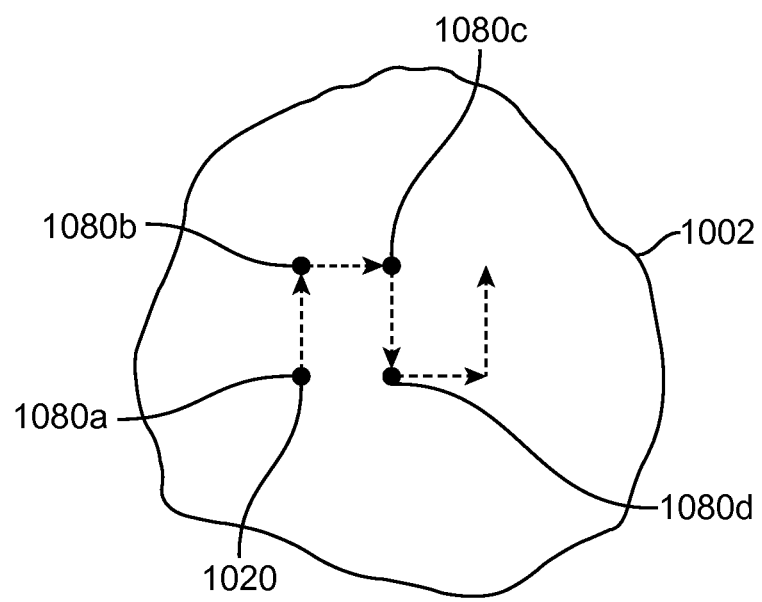
FIG. 10D illustrates a technique of scanning a pencil beam in accordance with some embodiments.

FIG. 10D illustrates a technique of scanning a volume of the target 1002 using a pencil beam 1020. First, the pencil beam 1020 is aimed towards the target 1002 to scan a first line/region 1080a of the target 1002. The radiation source 1004 then delivers a second pencil beam 1020 to scan a second line/region 1080b of the target 1002. The combination of the first and second beams 1020 results in a plane of the target 1002 being scanned. Next, the radiation source 1004 delivers a third pencil beam 1020 to scan a third line/region 1080c of the target 1002, and a fourth pencil beam 1020 to scan a fourth line/region 1080d of the target 1002. The combination of the third and second beams 1020 results in another plane of the target 1002 being scanned. The above process may be repeated to scan a volume of the target 1002. In some embodiments, the plurality of pencil beams 1020 may be provided by steering a beam aiming of the radiation source 1004. In other embodiments, the radiation source 1004 may be coupled to a positioner, which moves the radiation source 1004 to thereby deliver pencil beams at different regions of the target 1002. In further embodiments, a collimator may be placed between the radiation source 1004 and the target 1002 to collimate radiation provided by the source 1004 into a sequence of pencil beams 1020 that are delivered to different parts of the target 1002.

In one or more embodiments described herein, the apparatus 1000 may optionally further include a collimator placed between the radiation source 1004 and the target 1002. Such collimator may be used to collimate the first beam 1020 before it reaches the target 1002. In some embodiments, the radiation source 1004 may provide a cone beam, and the collimator may collimate the cone beam into a single pencil beam, multiple pencil beams, a single fan beam, or multiple fan beams. In other embodiments, the radiation source 1004 may provide a fan beam, and the collimator may collimate the fan beam into a single pencil beam, or multiple pencil beams. In some embodiments, the collimator may be considered to be a part of the radiation source 1004.

Figure 11A:
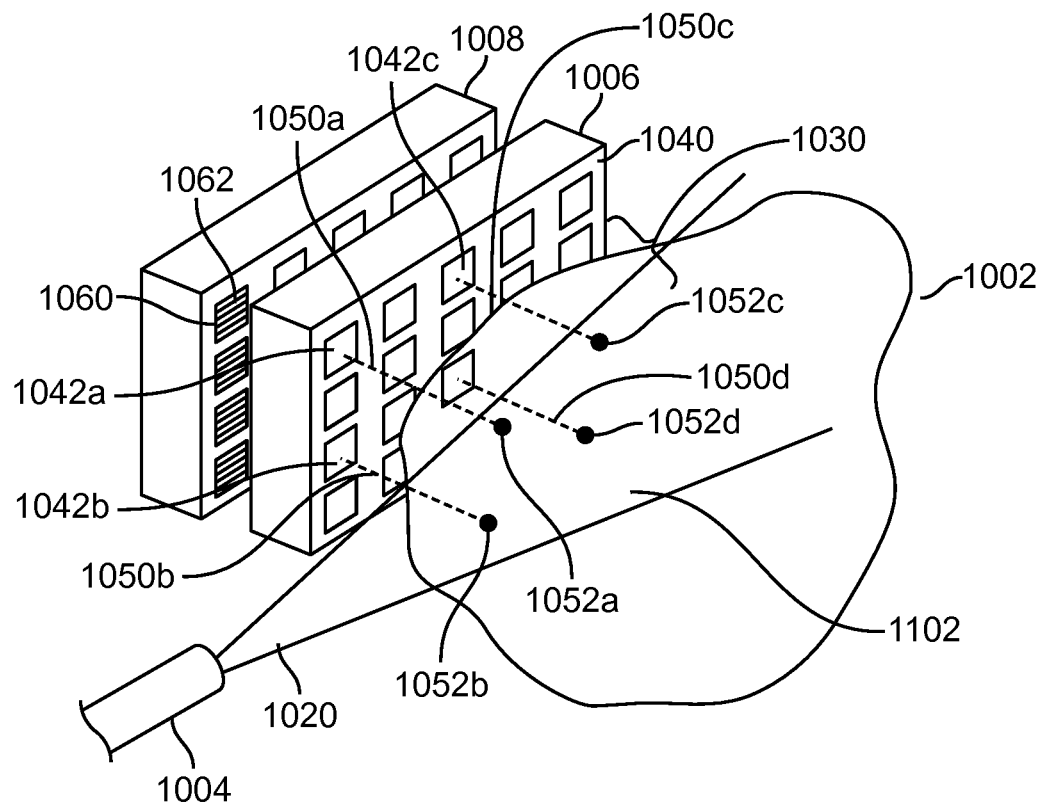
FIG. 11A illustrates another apparatus for examining a target in accordance with other embodiments.

In the above embodiments, the apparatus 1000 has been described with reference to the radiation source 1004 generating a pencil beam. In other embodiments, the radiation source 1004 may provide a fan beam or a cone beam. For example, as shown in FIG. 11A, the radiation source 1004 provides a fan beam 1020 towards the target 1002 for scanning a plane region 1102 of the target 1002. The fan beam 1020 interacts with a plane region 1102 of the target 1002 to create second beam 1030. As shown in the figure, the second beam 1030 includes different portions 1050a-1050d resulted from interaction of the beam 1020 with corresponding parts 1052a-1052d of the target 1002. The beam portions 1050a-1050d are collimated by the collimation device 1006 before they are detected by the detector 1008.

In the illustrated embodiments, the collimation device 1006 includes walls 1040 defining a plurality of openings 1042. Each opening 1042 has a square cross section. In other embodiments, each opening 1042 may have a rectangular cross section, a circular cross section, or other cross sectional shapes. As shown in the figure, the openings 1042 are arranged in an array having rows and columns. Such configuration allows collimation of the second beam 1030 into respective collimated beam portions arranged in a two-dimensional array. In particular, as shown in FIG. 11A, the first portion 1050a of the second beam 1030 is collimated by the device 1006 so that a part of it that travels substantially perpendicular towards the device 1006 will go through the device 1006 (e.g., through the opening 1042a), with the remaining part (e.g., the diverging part) being blocked by the walls 1040 of the device 1006. Similarly, the second portion 1050b of the second beam 1030 is collimated by the device 1006 so that a part of it that travels substantially perpendicular towards the device 1006 will go through the device 1006 (e.g., through the opening 1042b), with the remaining part (e.g., the diverging part) being blocked by the walls 1040 of the device 1006. Similarly, the third portion 1050c of the second beam 1030 is collimated by the device 1006 so that a part of it that travels substantially perpendicular towards the device 1006 will go through the device 1006 (e.g., through the opening 1042c), with the remaining part (e.g., the diverging part) being blocked by the walls 1040 of the device 1006. Similarly, the fourth portion 1050d of the second beam 1030 is collimated by the device 1006 so that a part of it that travels substantially perpendicular towards the device 1006 will go through the device 1006 (e.g., through the opening 1042d), with the remaining part (e.g., the diverging part) being blocked by the walls 1040 of the device 1006.

As shown in FIG. 11A, the detector 1008 includes a plurality of detector elements 1060 that are aligned with respective openings 1042 of the collimation device 1006. Each detector element 1060 includes six sub-detector elements (channels) 1062. In other embodiments, each detector element 1060 may include more than six channels, or fewer than six channels. The detector elements 1060 are arranged in a plurality of rows and columns that correspond with the configuration of the openings 1042 at the collimation device 1006.

Following the above example, after the first portion 1050a of the second beam 1030 has been collimated by the device 1006, the first portion 1050a of the second beam 1030 exits from the other side of the device 1006 to reach the corresponding detector elements 1060 that are aligned with the opening 1042a. Similarly, after the second portion 1050b of the second beam 1030 has been collimated by the device 1006, the second portion 1050b of the second beam 1030 exits from the other side of the device 1006 to reach the corresponding detector elements 1060 that are aligned with the opening 1042b. Similarly, after the third portion 1050c of the second beam 1030 has been collimated by the device 1006, the third portion 1050c of the second beam 1030 exits from the other side of the device 1006 to reach the corresponding detector elements 1060 that are aligned with the opening 1042c. Similarly, after the fourth portion 1050d of the second beam 1030 has been collimated by the device 1006, the fourth portion 1050d of the second beam 1030 exits from the other side of the device 1006 to reach the corresponding detector elements 1060 that are aligned with the opening 1042d.

For each beam portion 1050 that has exited the device 1006 and detected by the detector element 1060, the detector element 1060 detects the energy counts that are associated with that beam portion 1050. In some embodiments, the energy counts from each detector element 1060 (corresponding to a respective one of the collimator openings 1042) may be used to create an energy spectrum 1070, such as that described with reference to FIG. 10O. In the illustrated example, the four opening 1042a-1042d at the collimation device 1006 will result in four corresponding energy spectrums 1070 for the four respective parts 1052a-1052d of the target 1002.

Although only four parts 1052a-1052d of the target 1002 are illustrated, and two corresponding energy spectrums 1070 are described, it should be understood that the target 1002 may have more than four parts 1052, and that in other embodiments, the detector 1008 may provide more than four energy spectrums 1070 that corresponding to different parts of the target 1002. For example, in other embodiments, if the collimation device 1006 has twenty openings 1042, there may be twenty corresponding energy spectrums 1070 corresponding to different parts 1052 of the target 1002.

In some embodiments, the user interface 1010 may include a processing unit configured to process information from the energy spectrums 1070. For example, in some embodiments, the processing unit may be configured to calculate a ratio V, a ratio E, or other parameters, as similarly discussed with reference to FIG. 10C. In other embodiments, the processing unit may be configured to create a model using signals provided by the detector 1008. For example, in other embodiments, the processing unit may be configured to create a model showing functional and/or temporal characteristics of different parts of the target 1002. In some embodiments, the model may be a two dimensional model corresponding to different parts 1052 of the target 1002 in the plane 1102. In other embodiments, the model may be a three dimensional model corresponding to different parts 1052 of the target 1002 in a volume (e.g., in a plurality of planes 1102, as will be described in further detail with reference to FIG. 11B below).

In one or more embodiments described herein, the apparatus 1000 may optionally further include a collimator placed between the radiation source 1004 and the target 1002. Such collimator may be used to collimate the first beam 1020 before it reaches the target 1002. For example, in some embodiments, the radiation source 1004 may provide a fan beam, and the collimator may collimate the fan beam into a plurality of pencil beams. In such cases, the pencil beams will simultaneously interact with parts of the target 1002 that are in the plane 1102. In one implementation, the collimator may be a device having a single row of openings for collimating the beam 1020 into a plurality of pencil beams. In some embodiments, the collimator may be considered to be a part of the radiation source 1004.

Figure 11B:
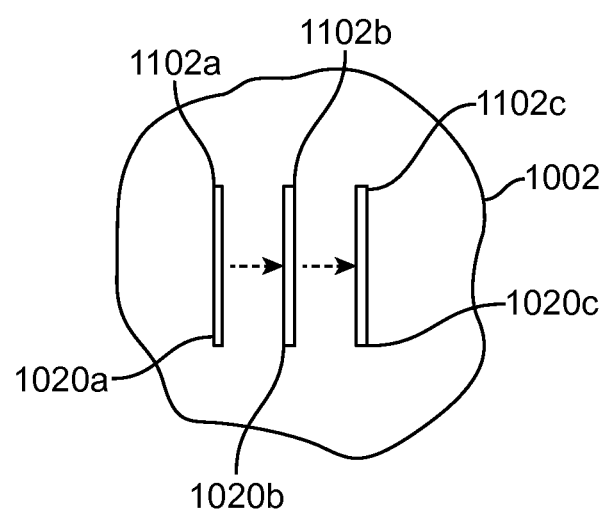
FIG. 11B illustrates a technique of scanning a fan beam in accordance with some embodiments.

In some embodiments, the radiation source 1004 may deliver a plurality of fan beams to scan a volume of the target 1002. For example, as shown in FIG. 11B, in some embodiments, the radiation source 1004 may provide a first fan beam 1020a to scan a first plane region 1102a of the target. The radiation source then provides a second fan beam 1020b to scan a second plane region 1102b of the target, and a third fan beam 1020c to scan a third plane region 1102c of the target. The plurality of the fan beams 1020 result in a volume of the target 1002 being scanned. Although three fan beams 1020a-1020c are shown, in other embodiments, there may be more than three fan beams 1020, or fewer than three fan beams 1020. In some embodiments, the plurality of fan beams 1020 may be provided by steering a beam aiming of the radiation source 1004. In other embodiments, the radiation source 1004 may be coupled to a positioner, which moves the radiation source 1004 to thereby deliver fan beams at different plane regions 1102 of the target 1002. In further embodiments, a collimator may be placed between the radiation source 1004 and the target 1002 to collimate radiation provided by the source 1004 into a sequence of fan beams 1020 that are delivered to different parts of the target 1002.

In further embodiments, each beam 1020 in FIG. 11B may be a plurality of pencil beams 1020 that are collimated by a collimator placed between the radiation source 1004 and the target 1002. In such cases, the scanning of the target 1002 may be accomplished by delivering a first array 1020a of pencil beams, a second array 1020b of pencil beams, and a third array 1020c of pencil beams. Although three arrays 1020a-1020c are shown, in other embodiments, there may be more than three arrays 1020, or fewer than three arrays 1020.

Figure 12:
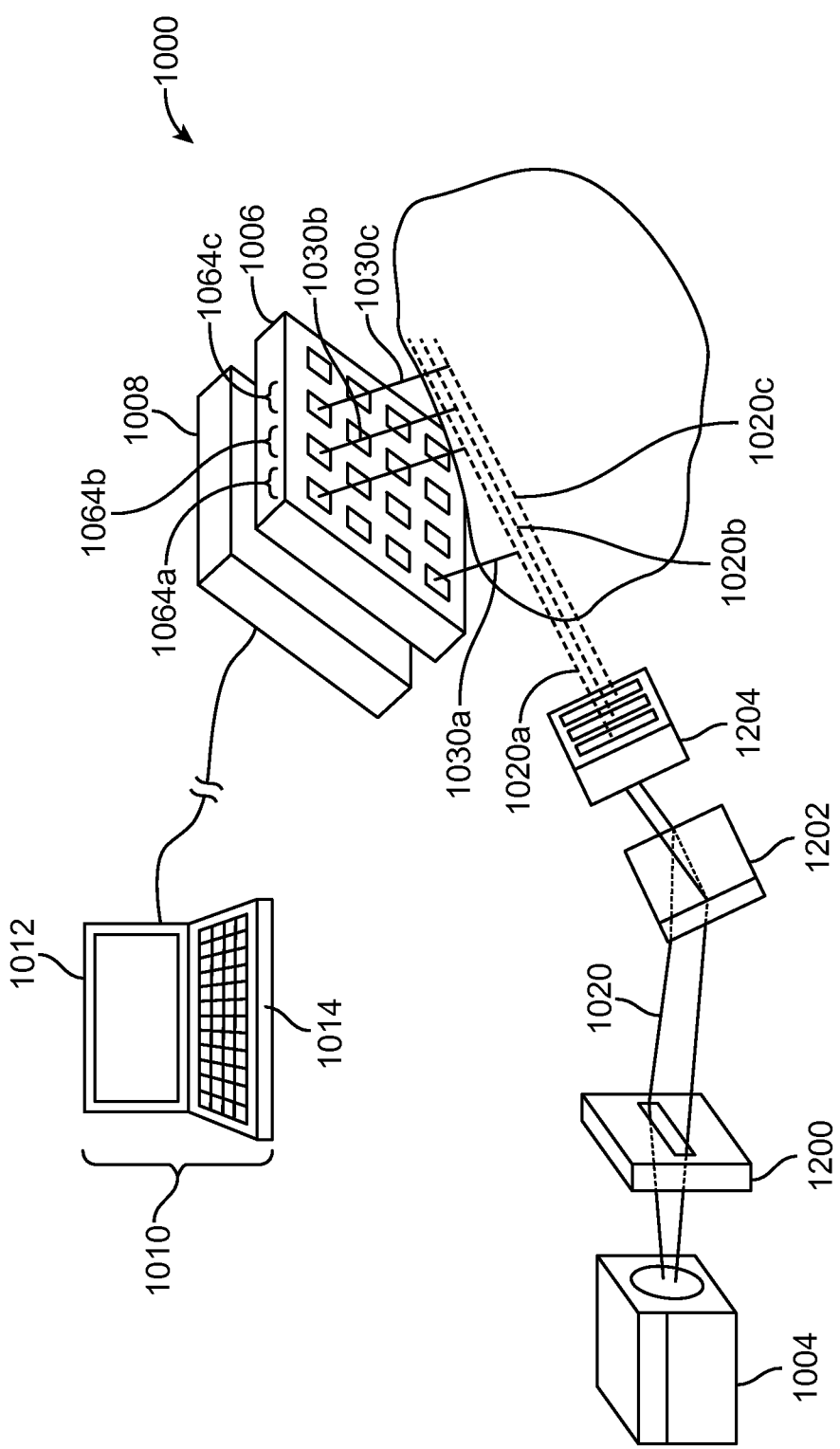
FIG. 12 illustrates another apparatus for examining a target in accordance with other embodiments.

It should be noted that the apparatus 1000 is not limited to the examples of configuration described, and that the apparatus 1000 may have other configurations in other embodiments. FIG. 12 illustrates a variation of the apparatus 1000 in accordance with some embodiments. The apparatus 1000 includes a radiation source 1004 for providing radiation, a first collimator 1200 for blocking some of the radiation to provide a fan beam 1020, a crystal 1202 for defracting the beam 1020, a second collimator 1204 for collimating the defracted beam 1020 into a plurality of pencil beams 1020a-1020c. In the illustrated embodiments, the crystal 1202 is a Germanium crystal configured to defract x-ray of certain energy (e.g., 40 keV). In other embodiments, the crystal 1202 may be other materials, and/or may be configured to defract x-ray at other energy levels. In some embodiments, the crystal 1202 is configured to produce incident quanta that have a certain specific energy (e.g., mono energetic x-rays, quasi mono energetic x-rays, etc.). Techniques for determining the angle of placement for a crystal get high reflectivity for a particular energy (mono energetic x-rays) are well known in the art. As used in this specification, the term "mono energetic x-ray" or similar terms is not limited to x-ray having a single energy level, and may refer to x-ray that is quasi mono energetic (e.g., x-ray having some spread of energy range, with a certain center energy). Although three pencil beams 1020a-1020c are shown, in other embodiments, there may be more than three pencil beams 1020, or fewer than three pencil beams 1020.

In the illustrated embodiments, the first pencil beam 1020a interacts with different parts of the target 1002 along the axis of the first pencil beam 1020a to generate second beam 1030a. The second beam 1030a is collimated by the corresponding column 1064a of openings 1042 so that the second beam 1030a exits the collimation device 1006 in the form of multiple isolated beams. The multiple isolated beams are then detected by corresponding detector elements 1060 at the detector 1008. Similarly, the second pencil beam 1020b interacts with different parts of the target 1002 along the axis of the second pencil beam 1020b to generate beam 1030b. The beam 1030b is collimated by the corresponding column 1064b of openings 1042 so that the beam 1030b exits the collimation device 1006 in the form of multiple isolated beams. The multiple isolated beams are then detected by corresponding detector elements 1060 at the detector 1008. Similarly, the third pencil beam 1020c interacts with different parts of the target 1002 along the axis of the third pencil beam 1020c to generate beam 1030c. The beam 1030c is collimated by the corresponding column 1064c of openings 1042 so that the beam 1030c exits the collimation device 1006 in the form of multiple isolated beams. The multiple isolated beams are then detected by corresponding detector elements 1060 at the detector 1008.

In the illustrated embodiments, signals from the detector 1008 may be transmitted to the user interface 1010. In some embodiments, a processing unit at the user interface 1010 may process the signals, and displayed the processed signals at the screen 1012. For example, the processing unit may be configured to calculate a ratio V, a ratio E, or other parameters, as similarly discussed with reference to FIG. 10C, and/or perform other functions as describe herein. In other embodiments, the signals from the detector 1008 may be stored in a non-transitory medium for later processing.

Embodiments of the apparatus 1000 described herein may be used to examine a variety of targets, including but not limited to tissue (with or with an agent, such as a contrast agent, a radioactive agent, etc.), objects in a luggage for suspicious items, non-destructive testing in industrial application (e.g., to detect corrosion, cracks, etc.). For example, in some embodiments, methods described herein may be used to measure characteristic(s) in non-tissue objects with the use of dyes or naturally occurring high Z elements. In medical applications, embodiments of the apparatus 100 described herein may be used to perform non-invasive biopsy, e.g., to detect fast growing substance, such as cancer. In some embodiments, a rate of growth of a substance may be correlated with a parameter derived from data in the energy spectrum 1070. In other embodiments, the apparatus 1000 may be used to detect any medical-related substance or condition, such as hypoxia, mesthesis, etc. For example, the processing unit of the apparatus 1000 may be configured to identify, based on signals received from the detector 1008, an agent that attaches to oxygen. In other embodiments, the processing unit of the apparatus 1000 may be configured to identify a marker for any medical condition. In still further embodiments, based on signals received from the detector 1008, the processing unit of the apparatus 1000 may be configured to identify/measure density of agent attached to a cancer site, angiogenesis, hypoxia, effectiveness of radiation treatment, pathological functional markers or identifiers of cancer malignancy, identifiers or cancer growth and growth rate, radiation treatment progress during treatment, lack of radiation treatment progress during treatment, properties of tissue environment surrounding an agent. Also, in one or more embodiments described herein, the target may be a liver, a kidney, a breast, a thyroid, or any bodily region. In such cases, based on signals received from the detector 1008, the processing unit of the apparatus 1000 may be configured to perform in situ non-invasive biopsy of any of these tissues. In further embodiments, based on signals received from the detector 1008, the processing unit of the apparatus 1000 may be configured to measure properties of tissue environment surrounding an agent (e.g., contrast agent, tissue) that is being examined. In one or more embodiments, the processing unit may be configured to process signals from the detector 1008 to determine information regarding one or more of the above features. For example, the processing unit may be configured to process signals from the detector 1008 to identify one or more peaks in a spectrum, determine peak value(s) for the respective peak(s), and perform calculation using the peak value(s). By means of non-limiting examples, the calculation using the peak value(s) may involve calculating ratio(s) using the peak values, performing normalization, comparing peak value(s) with one or more other peak values (which may be reference peak value(s)), etc. In some embodiments, a result of the calculation may be used to correlate with one or more of the features (properties) described above, such as a density of agent attached to a cancer site, angiogenesis, hypoxia, radiation treatment effectiveness, pathological functional marker(s), an identifier of cancer malignancy, an identifier of cancer growth, an identifier of cancer growth rate, a progress of radiation treatment, lack of a progress of radiation treatment, tissue property, or a property of an environment surrounding an agent in tissue.

In further embodiments, the processing unit of the apparatus 1000 may be configured to determine density of at least a portion of the target 1002 using signals from the detector 1008. The density measurement may be performed at high rate, and/or in real time. In one or more embodiments described herein, the detector 1008 may obtain energy counts sufficient to generate the energy spectrum 1070 within a very short duration, such as one second, or less. Thus, in one or more embodiments described herein, the apparatus 1000 may be used to obtain measurement (e.g., fluid build up, retention, leakage, density, etc.) in real time for medical purposes. In other embodiments, the apparatus 1000 may be used to obtain other types of functional information, pathological information, or other types of medical information.

As described herein, information from the detector may be analyzed to obtain one or more properties of the target being examined. In some embodiments, a processor may be configured (e.g., built and/or programmed to include an algorithm) to consider information related to Compton scatter (e.g. from one or more directions) and/or one, two, three, or more k x-ray from one or more agents which may be already present in the target or may be introduced into the target. In some embodiments, the relative intensities and/or their energies or other properties related to the Compton scatter and k-ray may be analyzed to obtain information related to functional and/or physical properties of voxels in the target. For example, in some embodiments, measurement of Compton peak may correlate with (and therefore may be used to indicate) the electron density of the voxel. In other embodiments, measurement of one k-peak and one Compton peak may be used to determine density and amount of agent in the voxel. In further embodiments, time synchronized measurement of information may be used to determine (e.g., indicate or measure) information about the flow of substance (e.g., agent) into or out of the voxel. Also, in some embodiments, acquisition of data related to two, three or more Compton or k x-ray may be used to determine (e.g., indicate or measure) environment properties of the voxel or its surroundings, such as, the environment's electronic spectrum, its atomic structure and or lattice spacing.

In one or more embodiments described herein, the apparatus 1000 may be implemented as an office-size unit. In other embodiments, the apparatus 1000 may be implemented as a hospital mobile unit. In further embodiments, the apparatus 1000 may be implemented as a unit for radiation oncology. In still further embodiments, the apparatus 1000 may be implemented as a full capability unit. In other embodiments, the apparatus 1000 may be implemented as a hand held device.

It should be noted that the system and method for examining an object described above are not limited to using x-ray, and that similar techniques may be implemented using other imaging modalities. For example, the object examination techniques described herein may be implemented using a PET system, a CT system (such as a CBCT system), a nuclear imaging system, a magnetic resonance imaging system, a line scan imaging system, etc.

As illustrated in some of the above embodiments, systems and methods described herein may be used for determination of pathological and functional information about cells and tissue without physical removal of their biological site. This in situ biopsy information can provide knowledge of extreme importance in medical care and treatment of numerous diseases. In some embodiments, the in situ measurement of pathological and functional information about small nodules of tissue at points in space and time provides knowledge valuable in medical care, such as disease nature, size of disease, severity, change in pathology over time, prognosis, treatment, treatment effectiveness, necessity for change in treatment, etc. Also, embodiments of the systems and methods described herein for in situ biopsy provide measurement of pathological and functional properties which is not possible with invasive biopsy (where tissue is removed), and also not possible with existing imaging techniques (e.g., PET, CT, SPECT, MRI, etc.).

Computer System Architecture

Figure 13:
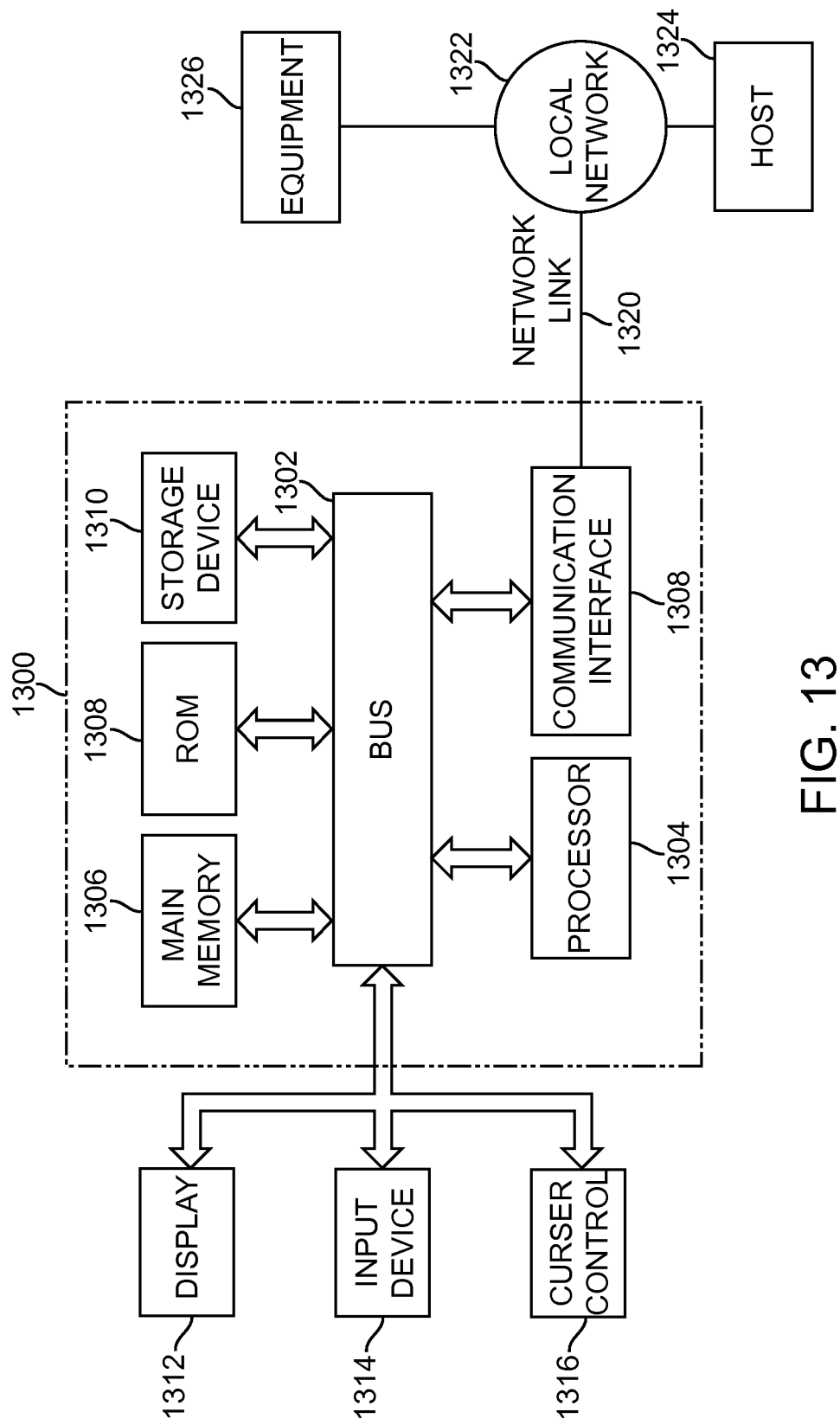
FIG. 13 illustrates a computer system with which embodiments described herein may be implemented.

FIG. 13 is a block diagram that illustrates an embodiment of a computer system 1300 upon which embodiments described herein may be implemented. For example, in some embodiments, the computer system 1300 may be used to process information obtained from the detector 1008. In some embodiments, the computer system 1300 may be used to implement the user interface 1010 of FIG. 10A.

Computer system 1300 includes a bus 1302 or other communication mechanism for communicating information, and a processor 1304 coupled with the bus 1302 for processing information. The processor 1304 may be configured to perform various functions described herein. The computer system 1300 also includes a main memory 1306, such as a random access memory (RAM) or other dynamic storage device, coupled to the bus 1302 for storing information and instructions to be executed by the processor 1304. The main memory 1306 also may be used for storing temporary variables or other intermediate information during execution of instructions to be executed by the processor 1304. The computer system 1300 further includes a read only memory (ROM) 1308 or other static storage device coupled to the bus 1302 for storing static information and instructions for the processor 1304. A data storage device 1310, such as a magnetic disk or optical disk, is provided and coupled to the bus 1302 for storing information and instructions.

The computer system 1300 may be coupled via the bus 1302 to a display 1312, such as a cathode ray tube (CRT) or a flat panel, for displaying information to a user. An input device 1314, including alphanumeric and other keys, is coupled to the bus 1302 for communicating information and command selections to processor 1304. Another type of user input device is cursor control 1316, such as a mouse, a trackball, or cursor direction keys for communicating direction information and command selections to processor 1304 and for controlling cursor movement on display 1312. This input device typically has two degrees of freedom in two axes, a first axis (e.g., x) and a second axis (e.g., y), that allows the device to specify positions in a plane.

The computer system 1300 may be used for performing various functions (e.g., calculation) in accordance with the embodiments described herein. According to one embodiment, such use is provided by computer system 1300 in response to processor 1304 executing one or more sequences of one or more instructions contained in the main memory 1306. Such instructions may be read into the main memory 1306 from another computer-readable medium, such as storage device 1310. Execution of the sequences of instructions contained in the main memory 1306 causes the processor 1304 to perform the process steps described herein. One or more processors in a multi-processing arrangement may also be employed to execute the sequences of instructions contained in the main memory 1306. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 1304 for execution. Such a medium may take many forms, including but not limited to, non-volatile media, volatile media, and transmission media. Non-volatile media (an example of non-transitory media) includes, for example, optical or magnetic disks, such as the storage device 1310. Volatile media (another example of non-transitory media) includes dynamic memory, such as the main memory 1306. Transmission media includes coaxial cables, copper wire and fiber optics, including the wires that comprise the bus 1302. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1304 for execution. For example, the instructions may initially be carried on a magnetic disk of a remote computer. The remote computer can load the instructions into its dynamic memory and send the instructions over a telephone line using a modem. A modem local to the computer system 1300 can receive the data on the telephone line and use an infrared transmitter to convert the data to an infrared signal. An infrared detector coupled to the bus 1302 can receive the data carried in the infrared signal and place the data on the bus 1302. The bus 1302 carries the data to the main memory 1306, from which the processor 1304 retrieves and executes the instructions. The instructions received by the main memory 1306 may optionally be stored on the storage device 1310 either before or after execution by the processor 1304.

The computer system 1300 also includes a communication interface 1318 coupled to the bus 1302. The communication interface 1318 provides a two-way data communication coupling to a network link 1320 that is connected to a local network 1322. For example, the communication interface 1318 may be an integrated services digital network (ISDN) card or a modem to provide a data communication connection to a corresponding type of telephone line. As another example, the communication interface 1318 may be a local area network (LAN) card to provide a data communication connection to a compatible LAN. Wireless links may also be implemented. In any such implementation, the communication interface 1318 sends and receives electrical, electromagnetic or optical signals that carry data streams representing various types of information.

The network link 1320 typically provides data communication through one or more networks to other devices. For example, the network link 1320 may provide a connection through local network 1322 to a host computer 1324 or to equipment 1326 such as a radiation beam source or a switch operatively coupled to a radiation beam source. The data streams transported over the network link 1320 can comprise electrical, electromagnetic or optical signals. The signals through the various networks and the signals on the network link 1320 and through the communication interface 1318, which carry data to and from the computer system 1300, are exemplary forms of carrier waves transporting the information. The computer system 1300 can send messages and receive data, including program code, through the network(s), the network link 1320, and the communication interface 1318.

Those skilled in the art will appreciate that various other modifications may be made within the spirit and scope of the claimed invention. All these or other variations and modifications are contemplated by the inventors and within the scope of the claimed invention.

What is claimed is:

1. An apparatus to examine a target, comprising:
an x-ray source configured to deliver a first x-ray beam towards the target;
a device having an array of openings, wherein at least two of the openings are next to each other in a side-by-side configuration, the device located at an angle less than 180 degrees relative to a beam path of the first x-ray beam to receive a second x-ray beam resulted from an interaction between the first x-ray beam and the target; and a detector aligned with the device, the detector located at an angle less than 180 degrees relative to the beam path of the first x-ray beam to receive the second x-ray beam from the device after the second x-ray beam has exited through one or more of the openings of the device;

wherein the apparatus further comprises a processing unit configured to:
determine two or more peaks based on data received from the detector, the two or more peaks selected from the group consisting of a first k-alpha peak, a first k-beta peak, a first Compton scatter peak, a second k-alpha peak, a second k-beta peak, and a second Compton scatter peak, and
calculate a parameter indicating a cancer characteristic, wherein the processing unit is configured to calculate the parameter by computing a ratio between two of the two or more peaks.

2. The apparatus of claim 1, wherein the detector comprises a first detector element and a second detector element, the first detector element corresponding with a first one of the openings, the second detector element corresponding with a second one of the openings; and
wherein the first detector element is configured to provide spectrum data in response to the first beam interacting with a first part of the target, and the second detector element is configured to provide second spectrum data in response to the first beam interacting with a second a second part of the target.

3. The apparatus of claim 1, wherein the processing unit configured to determine examination data based on signals generated by the detector, the examination data representing fluid build up, fluid retention, fluid wash out, rate of fluid build up, or rate of fluid wash out.

4. The apparatus of claim 1, further comprising an image re-constructor for reconstructing a volumetric image of the target using signals generated by the detector.

5. The apparatus of claim 1, wherein the angle is a value that is anywhere between 30 degrees and 170 degrees.

6. The apparatus of claim 1, wherein the second beam comprises a photo absorption component and a Compton scatter component.

7. The apparatus of claim 1, further comprising a collimator between the x-ray source and the target.

8. The apparatus of claim 1, wherein the detector comprises a photo spectrum sensitive detector.

9. The apparatus of claim 1, wherein each of the openings has an elongated shape.

10. The apparatus of claim 1, wherein the openings are arranged in a plurality of rows.

11. The apparatus of claim 1, wherein the device comprises a plurality of spaced apart plates that define the array of openings.

12. The apparatus of claim 1, wherein the first x-ray beam comprises a cone beam.

13. The apparatus of claim 1, wherein the first x-ray beam comprises a first fan beam for examining parts of the target that are in a first plane.

14. The apparatus of claim 13, wherein the x-ray source is configured to provide a second fan beam for examining parts of the target that are in a second plane.

15. The apparatus of claim 1, wherein the first x-ray beam comprises a first pencil beam for examining parts of the target that are along a first line.

16. The apparatus of claim 15, wherein the x-ray source is configured to provide a second pencil beam for examining parts of the target that are along a second line, the first line and the second line defining a plane.

17. The apparatus of claim 16, wherein the x-ray source is configured to provide a third pencil beam for examining parts of the target that are along a third line.

18. The apparatus of claim 1, wherein the parameter comprises information regarding a density of agent attached to a cancer site, information regarding angiogenesis, information regarding hypoxia, information regarding pathological functional marker(s), information regarding an identifier of cancer malignancy, information regarding an identifier of cancer growth, or information regarding an identifier of cancer growth rate.

19. The apparatus of claim 1, wherein the second x-ray beam has a first beam portion and a second beam portion travelling in different respective directions, and wherein the device is configured to allow the first beam portion to go through the one or more of the openings, and block the second beam portion.

20. The apparatus of claim 1, wherein the angle is approximately 90 degrees.

21. The apparatus of claim 1, wherein the angle is anywhere from 30 degrees to 100 degrees.

22. The apparatus of claim 1, wherein the processing unit is configured to calculate the parameter using an intensity of the first k-alpha peak, an intensity of the first k-beta peak, an intensity of the first Compton scatter peak, or two or more of the foregoing.

23. The apparatus of claim 1, wherein the processing unit is configured to calculate the parameter using an area under the first k-alpha peak, an area under the first k-beta peak, an area under the first Compton scatter peak, or two or more of the foregoing.

24. The apparatus of claim 1, wherein the processing unit is also configured to determine information regarding radiation treatment effectiveness, information regarding a progress of radiation treatment, or information regarding lack of a progress of radiation treatment.

25. An apparatus to examine a target, comprising:
an x-ray source configured to deliver a first x-ray beam towards the target;
a device having an array of openings, wherein at least two of the openings are next to each other in a side-by-side configuration, the device located at an angle less than 180 degrees relative to a beam path of the first x-ray beam to receive a second x-ray beam resulted from an interaction between the first x-ray beam and the target; and
a detector aligned with the device, the detector located at an angle less than 180 degrees relative to the beam path of the first x-ray beam to receive the second x-ray beam from the device after the second x-ray beam has exited through one or more of the openings of the device;
wherein the apparatus further comprises a processing unit configured to:
determine two or more peaks based on data received from the detector, the two or more peaks selected from the group consisting of a first k-alpha peak, a first k-beta peak, a first Compton scatter peak, a second k-alpha peak, a second k-beta peak, and a second Compton scatter peak, and
calculate a parameter indicating a cancer characteristic by computing a ratio between two of the two or more peaks; and
wherein the openings are arranged in a plurality of rows, and wherein each of the plurality of rows has multiple ones of the openings.

26. A method to image a target, comprising:
directing a first x-ray beam generated from an x-ray source towards the target, wherein a second x-ray beam is generated by an interaction of the first x-ray beam with the target;
using a device with an array of openings to collimate the second x-ray beam wherein at least two of the openings are next to each other in a side-by-side configuration;
after the second x-ray beam has been collimated by the device, detecting the second x-ray beam using a detector that is placed at an angle less than 180 degrees relative to a path of the first x-ray beam; and
obtaining quantum property for the target using the detected second x-ray beam;
wherein the method further comprises:
determining two or more peaks based on data received from the detector, the two or more peaks selected from the group consisting of a first k-alpha peak, a first k-beta peak, a first Compton scatter peak, a second k-alpha peak, a second k-beta peak, and a second Compton scatter peak, and
calculating a parameter indicating cancer characteristic, wherein the act of calculating the parameter comprises computing a ratio between two of the two or more peaks.

27. The method of claim 26, wherein the act of obtaining the quantum property comprises obtaining first energy spectrum data for a first part of the target and second energy spectrum data for a second part of the target.

28. The method of claim 26, wherein the second x-ray beam comprises a first portion and a second portion, wherein the act of using the device to collimate the second x-ray beam comprises collimating the second x-ray beam so that the first portion of the second x-ray beam is allowed to travel towards a first part of the detector, and the second portion of the second x-ray beam is allowed to travel towards a second part of the detector.

29. The method of claim 26, further comprising determine examination data based on signals generated by the detector, the examination data representing fluid build up, fluid retention, fluid wash out, rate of fluid build up, or rate of fluid wash out.

30. The method of claim 26, further reconstructing a volumetric image of the target using signals generated by the detector.

31. The method of claim 26, wherein the angle is a value that is anywhere between 30 degrees and 170 degrees.

32. The method of claim 26, wherein the second x-ray beam comprises a photo absorption component and a Compton scatter component.

33. The method of claim 26, further comprising collimating the first x-ray beam before the first x-ray beam reaches the target.

34. The method of claim 26, wherein the detector comprises a photo spectrum sensitive detector.

35. The method of claim 26, wherein the first x-ray beam comprises a cone beam.

36. The method of claim 26, wherein the first x-ray beam comprises a first fan beam, the first beam interacting with a first part, a second part, and a third part of the target to produce a first portion, a second portion, and a third portion, respectively, of the second x-ray beam;
wherein the first part, the second part, and the third part of the target are in a first plane.

37. The method of claim 36, further comprising directing a second fan beam towards the target for examining parts of the target that are in a second plane.

38. The method of claim 26, wherein the first x-ray beam comprises a first pencil beam, the first pencil beam interacting with a first part of the target to produce a first portion of the second x-ray beam, and interacting with a second part of the target to produce a second portion of the second x-ray beam;
wherein the first part and the second part of the target are along a first line.

39. The method of claim 38, further comprising directing a second pencil beam towards the target for examining parts of the target along a second line.

40. The method of claim 39, further comprising directing a third pencil beam towards the target for examining parts of the target along a third line.

41. The method of claim 26, further comprising using the quantum property to determine temporal information regarding the target.

42. The method of claim 26, wherein the quantum property comprises energy spectrum data.

43. The method of claim 26, wherein the parameter comprises information regarding a density of agent attached to a cancer site, information regarding angiogenesis, information regarding hypoxia, information regarding pathological functional marker(s), information regarding an identifier of cancer malignancy, information regarding an identifier of cancer growth, or information regarding an identifier of cancer growth rate.

44. The method of claim 26, wherein the second x-ray beam has a first beam portion and a second beam portion travelling in different respective directions, and wherein the device is used to allow the first beam portion to go through one or more of the openings while blocking the second beam portion.

45. The method of claim 26, wherein the angle is approximately 90 degrees.

46. The method of claim 26, wherein the angle is anywhere from 30 degrees to 100 degrees.

47. An apparatus to examine a target, comprising:
an x-ray source configured to deliver a first x-ray beam towards the target;
a device having an array of openings, wherein at least two of the openings are next to each other in a side-by-side configuration, the device located at an angle less than 180 degrees relative to a beam path of the first x-ray beam to receive a second x-ray beam resulted from an interaction between the first x-ray beam and the target;
a detector aligned with the device, the detector located at an angle less than 180 degrees relative to the beam path of the first x-ray beam to receive the second x-ray beam from the device after the second x-ray beam has exited through one or more of the openings of the device; and
a processing unit configured to determine two or more peaks based on data from the detector, the two or more peaks selected from the group consisting of a first k-alpha peak, a first k-beta peak, a first Compton scatter peak, a second k-alpha peak, a second k-beta peak, and a second Compton scatter peak, and wherein the processing unit is configured to determine a parameter indicating a cancer characteristic by calculating a ratio between two of the two or more peaks.

48. The apparatus of claim 47, wherein the angle is approximately 90 degrees.

49. A method to image a target, comprising:
directing a first x-ray beam generated from an x-ray source towards the target, wherein a second x-ray beam is generated by an interaction of the first x-ray beam with the target;

using a device with an array of openings to collimate the second x-ray beam wherein at least two of the openings are next to each other in a side-by-side configuration;

after the second x-ray beam has been collimated by the device, detecting the second x-ray beam using a detector that is placed at an angle less than 180 degrees relative to a path of the first x-ray beam;

determining two or more peaks based on data from the detector, the two or more peaks selected from the group consisting of a first k-alpha peak, a first k-beta peak, a first Compton scatter peak, a second k-alpha peak, a second k-beta peak, and a second Compton scatter peak; and determining a parameter indicating a cancer characteristic by calculating a ratio between two of the two or more peaks.

50. The method of claim 49, wherein the angle is approximately 90 degrees.

* * * * *